(12) United States Patent
Fukuoka

(10) Patent No.: US 12,343,369 B2
(45) Date of Patent: *Jul. 1, 2025

(54) PHARMACEUTICAL COMPOSITION FOR USE IN INCREASING HAIR, MODIFYING SCALP OR SKIN, HEALING A WOUND, PROMOTING OSTEOGENESIS, OR MODIFYING HAIR

(71) Applicant: Hirotaro Fukuoka, Tokyo (JP)

(72) Inventor: Hirotaro Fukuoka, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 17/853,335

(22) Filed: Jun. 29, 2022

(65) Prior Publication Data

US 2022/0409688 A1 Dec. 29, 2022

Related U.S. Application Data

(63) Continuation of application No. 16/635,221, filed as application No. PCT/JP2018/047736 on Dec. 26, 2018, now Pat. No. 11,413,321.

(30) Foreign Application Priority Data

Dec. 26, 2017 (JP) .................................. 2017-249980

(51) Int. Cl.
| | | |
|---|---|---|
| A61K 36/48 | (2006.01) | |
| A61K 9/00 | (2006.01) | |
| A61K 9/70 | (2006.01) | |
| A61P 19/00 | (2006.01) | |

(52) U.S. Cl.
CPC ............ *A61K 36/48* (2013.01); *A61K 9/0014* (2013.01); *A61K 9/7007* (2013.01); *A61P 19/00* (2018.01)

(58) Field of Classification Search
None
See application file for complete search history.

(56) References Cited

U.S. PATENT DOCUMENTS

| | | |
|---|---|---|
| 4,910,224 A | 3/1990 | Habib et al. |
| 5,663,208 A | 9/1997 | Martin |
| 5,750,149 A | 5/1998 | Gobbi |
| 5,863,938 A | 1/1999 | Martin |
| 6,849,268 B2 | 2/2005 | Lasekan et al. |
| 2006/0051305 A1 | 3/2006 | Belinky et al. |
| 2006/0228429 A1 | 10/2006 | Laguna Granja et al. |
| 2006/0233738 A1 | 10/2006 | Miyata et al. |
| 2008/0096963 A1 | 4/2008 | Jean et al. |
| 2008/0206353 A1 | 8/2008 | Phillips |
| 2009/0263415 A1 | 10/2009 | Goino et al. |
| 2010/0021574 A1 | 1/2010 | Laguna Granja et al. |
| 2010/0022649 A1 | 1/2010 | Laguna Granja et al. |
| 2011/0177025 A1 | 7/2011 | Thanos et al. |
| 2012/0029078 A1 | 2/2012 | Hesslink, Jr. et al. |
| 2012/0129789 A1 | 5/2012 | Yoelin |
| 2012/0149775 A1 | 6/2012 | Ezure |
| 2013/0150328 A1 | 6/2013 | Sato et al. |
| 2014/0079657 A1 | 3/2014 | Resnick et al. |
| 2014/0142092 A1 | 5/2014 | Burk et al. |
| 2015/0216902 A1 | 8/2015 | Fardoussi |
| 2016/0256505 A1 | 9/2016 | Xing et al. |
| 2016/0361249 A1 | 12/2016 | Resnick et al. |
| 2017/0196797 A1 | 7/2017 | Kang et al. |
| 2017/0333410 A1 | 11/2017 | Babul |
| 2017/0360554 A1 | 12/2017 | Linderman et al. |
| 2019/0167725 A1 | 6/2019 | Park et al. |

FOREIGN PATENT DOCUMENTS

| | | | |
|---|---|---|---|
| CA | 2536354 | * | 1/2006 |
| CN | 101128208 A | | 2/2008 |
| CN | 104602683 A | | 5/2015 |
| CN | 106466327 A | | 3/2017 |
| CN | 107072933 A | | 8/2017 |
| DE | 10 2006 053 692 A1 | | 8/2007 |
| EP | 0 116 439 A2 | | 8/1984 |
| EP | 0 490 581 A1 | | 6/1992 |
| EP | 0 675 708 A1 | | 10/1995 |
| EP | 0 675 708 B1 | | 10/1995 |
| EP | 1 623 740 A1 | | 2/2006 |
| EP | 2 735 303 A1 | | 5/2014 |
| EP | 2 895 181 A1 | | 7/2015 |
| JP | 59-172410 A | | 9/1984 |
| JP | 62-265222 A | | 11/1987 |
| JP | 4-290813 A | | 10/1992 |
| JP | 8-505630 A | | 6/1996 |
| JP | 08505630 | * | 6/1996 |
| JP | 10-503200 A | | 3/1998 |

(Continued)

OTHER PUBLICATIONS

Moetaz El-Domyati, MD, et al., Multiple fractional erbium: yttrium-aluminum-garnet laser sessions for upper facial rejuvenation: clinical and hitological implications and expectations, Journal of Cosmetic Dermatology, 13, pp. 30-37.

James Varani, et al., Decreased Collagen Production in Chronologically Aged Skin, American Journal of Pathology, vol. 168, No. 6, Jun. 2006, 8 pages.

Combined Taiwanese Office Action and Search Report Issued on Jul. 5, 2023 in Taiwanese Patent Application No. 111143564, 6 pages.

Cornish J, et al. "Endocrinology" Published Nov. 2008, vol. 149, No. 11. pp. 5688-5695.

Canadian Office Action issued on Jun. 15, 2023 in Canadian Patent application No. 3,070.854, 6 pages.

(Continued)

*Primary Examiner* — Michael V Meller
(74) *Attorney, Agent, or Firm* — Oblon, McClelland, Maier & Neustadt, L.L.P.

(57) ABSTRACT

The present invention provides a pharmaceutical composition for use in increasing hair, modifying scalp or skin, healing a wound, promoting osteogenesis or modifying hair, the pharmaceutical composition comprising a therapeutically effective amount of a saturated fatty acid or a pharmaceutically acceptable salt thereof as an active ingredient.

14 Claims, 22 Drawing Sheets

Specification includes a Sequence Listing.

(56) References Cited

FOREIGN PATENT DOCUMENTS

| | | |
|---|---|---|
| JP | 2001-501576 A | 2/2001 |
| JP | 2005-179190 A | 7/2005 |
| JP | 2006-51 4943 A | 5/2006 |
| JP | 2006-520331 A | 9/2006 |
| JP | 2008-525319 A | 7/2008 |
| JP | 2011-528352 A | 11/2011 |
| JP | 2012-8045 A | 1/2012 |
| JP | 2013-523893 A | 6/2013 |
| JP | 2013-543010 A | 11/2013 |
| JP | 2014-208609 A | 11/2014 |
| JP | 2015-522651 A | 8/2015 |
| JP | 2015-535214 A | 12/2015 |
| JP | 2015-537028 A | 12/2015 |
| JP | 2017-21 4363 A | 12/2017 |
| KR | 10-2015-0056820 | 5/2015 |
| KR | 10-1918773 B1 | 11/2018 |
| KR | 10-2122614 B1 | 6/2020 |
| WO | WO 94/16675 A1 | 8/1994 |
| WO | WO 98/36759 A1 | 8/1998 |
| WO | WO 2006/066323 A1 | 6/2006 |
| WO | WO 2008/147228 A1 | 12/2008 |
| WO | WO 2009/149537 A1 | 12/2009 |
| WO | WO2011039637 A2 | 4/2011 |
| WO | WO 2011/081136 A1 | 7/2011 |
| WO | WO 2014/043304 A1 | 3/2014 |
| WO | WO 2015/101625 A1 | 7/2015 |
| WO | WO 2017/081259 A1 | 5/2017 |
| WO | WO 2017/081529 A1 | 5/2017 |
| WO | WO 2017/146468 A1 | 8/2017 |

OTHER PUBLICATIONS

Bourre et al., "Importance of exogenous saturated fatty acids during brain development and myelination in mice." Anni. Biol. anim. Bioch. Biophys., 1979, 19 (1B), pp. 173-180. https://doi.org/10.1051/md:19790205.

Hurley et al., "The Colloidal State as a Stimulus for Non-Allergic Epithelloid Granulomas: Experimental Studies in Man with Pure Sodium Stearate and Palmitate", Journal of Investigative Dermatology, Published 1859/10, vol. 33, No. 4, p. 203-220.

Alexander et al., "Osteal Macrophages Promote In Vivo Intramembranous Bone Healing in a Mouse Tibial Injury Model", Journal of Bone and Mineral Research, vol. 26, No. 7, Jun. 2011, pp. 1517-1532 (Total 17 pages).

Combined Chinese Office Action and Search Report issued on Dec. 5, 2022 in Chinese Patent Application No. 201880050803.4 (with translation of category of cited documents), 9 pages.

International Search Report issued on Mar. 25, 2019 in PCT/JP2018/047736 filed on Dec. 26, 2018, 5 pages.

Notice of Reasons for Refusal issued on Aug. 20, 2019 in Japanese Patent Application No. 2019-537016 (with English language translation), 15 pages.

Notice of Reasons for Refusal issued on Oct. 9, 2019 in Japanese Patent Application No. 2019-537016 (with English language translation), 10 pages.

Decision to Grant a Patent issued on Nov. 8, 2019 in Japanese Patent Application No. 2019-537016 (with English language translation), 6 pages.

Festa, E. et al., "Adipocyte Lineage Cells Contribute to the Skin Stem Cell Niche to Drive Hair Cycling," Cell, vol. 146, 2011, pp. 761-771.

Satoh, T. et al., "Critical role of Trib1 in differentiation of tissue-resident M2-like macrophages," Nature, vol. 495, 2013, pp. 524-528, 7 total pages.

Japanese Office Action issued Apr. 7, 2020 in Japanese Patent Application No. 2019-198071, 5 pages.

Atiyeh B S et al, Cosmetic Mesotherapy: Between Scientific Evidence, Science Fiction, and Lucrative Business, Aesth Plast Surg (2008) 32:842-849 (8 pages).

French Society of Mesotherapy, http://sfmesotheraple.com/en/What-is-that/default.asp?MenuActive=2, Jun. 7, 2009 (1 page).

Japanese Office Action issued Jun. 9, 2020 in Japanese Patent Application No. 2020-080412, 3 pages.

Notice of Allowance issued Aug. 25, 2020 in Japanese Patent Application No. 2020-080412, 3 pages.

Guney, S., et al., "Seed Lipids of the Miracle Fruit", Journal of Food Biochemistry, vol. 1, 1977, pp. 173-184.

Singaporean Office Action issued Mar. 21, 2021 in Singaporean Patent Application No. 11202000906Y, 10 pages.

Li, H-L., et al., "Crocodile Oil Enhances Cutaneous Burn Wound Healing and Reduces Scar Formation in Rats", Official Journal of the Society for Academic Emergency Medicine, 2012, pp. 265-273.

Extended European Search Report issued Sep. 24, 2021 in European Patent Application No. 18895326.9, 11 pages.

Combined Taiwanese Office Action and Search Report issued Sep. 10, 2021 in Taiwanese Patent Application No. 107147193 (with English translation), 5 pages.

Singaporean Office Action issued Dec. 21, 2021 in Singaporean Patent Application No. 11202000906Y, 7 pages.

Hain, J.R., "Subcutaneous Corn Oil Injections, Fat Embolization Syndrome, and Death", the American Journal of Forensic Medicine and Pathology, Dec. 31, 2009, vol. 30 No. 4, pp. 398-402.

"Woman Gets 15 years after Anti-aging Cooking-Oil Injections Killed Client", Fox News (2007), Retrieved from the internet: URL: https://www.foxnews.com/story/woman-gets-15-years-after-anti-aging-cooking-oil-injections-killed-client, Jan. 18, 2007, 3 pages.

Mary Ann Liebert, Inc., Publishers, "Final Report on the Safety Assessment of Oleic Acid, Lauric Acid, Palmitic Acid, Myristic Acid, and Stearic Acid", Journal of the American College of Toxicology, vol. 6, No. 3, May 1, 1987, pp. 321-401.

Office Action issued on Oct. 27, 2023, in corresponding Canadian Patent Application No. 3070854.

Combined Chinese Notice of Allowance and Search Report issued in corresponding Chinese Patent Application No. 201880050803.4 (with English Translation and English Translation of Category of Cited Documents), 7 pages.

Chinese Office Action issued on Sep. 8, 2023 in Chinese Patent Application No. 201880050803.4, 6 pages.

Cao, "Colostrum functional food", China Light Industry Press, Mar. 2000, 7 pages (with English translation).

Mcdonald et al., "Animal Nutrition", China Agricultural University Press, Feb. 2007, 12 pages (with English translation).

Office Action mailed on Apr. 30, 2024, in corresponding Korean Patent Application No. 10-2020-7002999 (with machine translation).

European Office Action issued May 23, 2023 in European Application No. 18 895 326.9, 5 pages.

* cited by examiner

CD31

BEFORE TREATMENT (1)

FIVE MONTHS AFTER TREATMENT (8)

CD34

BEFORE TREATMENT (6)

FIVE MONTHS AFTER TREATMENT (34)

V: Blood Vessel

PPARγ

BEFORE TREATMENT (8)

FIVE MONTHS AFTER TREATMENT (22)

CD68

BEFORE TREATMENT (4)

FIVE MONTHS AFTER TREATMENT (40)

CD163

BEFORE TREATMENT (7)

FIVE MONTHS AFTER TREATMENT (16)

H: Hair Follicle                    S: Sebaceous Gland

PHYSIOLOGICAL SALINE    PPARγ

| ADMINISTRATION LOCATION FOUR WEEKS AFTER ADMINISTRATION | ADMINISTRATION LOCATION EIGHT WEEKS AFTER ADMINISTRATION |
|---|---|
|  |  |
| (7) | (7) |

CD68

| ADMINISTRATION LOCATION FOUR WEEKS AFTER ADMINISTRATION | ADMINISTRATION LOCATION EIGHT WEEKS AFTER ADMINISTRATION |
|---|---|
|  |  |
| (9) | (10) |

FIG. 10B  PALMITIC ACID
PPARγ
ADMINISTRATION LOCATION FOUR WEEKS AFTER ADMINISTRATION
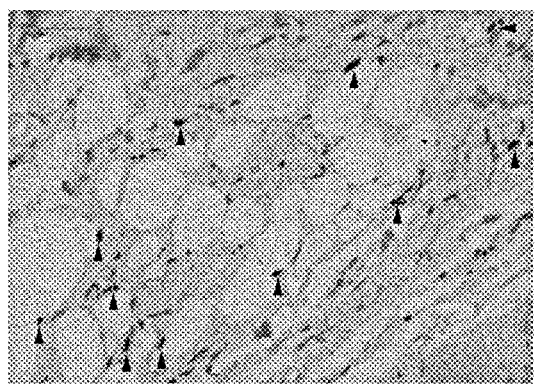
(11)
ADMINISTRATION LOCATION EIGHT WEEKS AFTER ADMINISTRATION
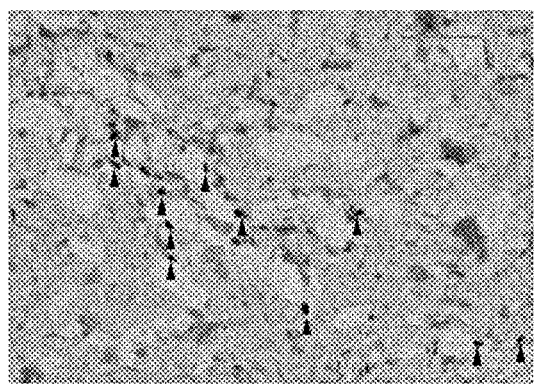
(11)
CD68
ADMINISTRATION LOCATION FOUR WEEKS AFTER ADMINISTRATION
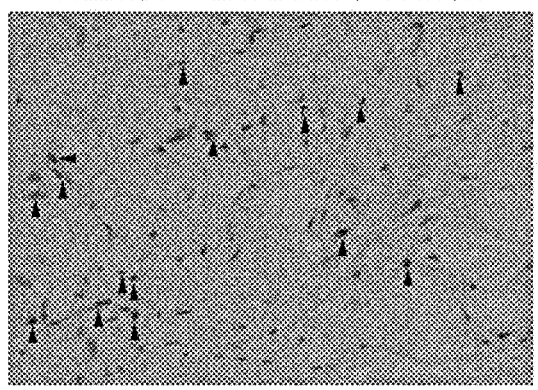
(15)
ADMINISTRATION LOCATION EIGHT WEEKS AFTER ADMINISTRATION
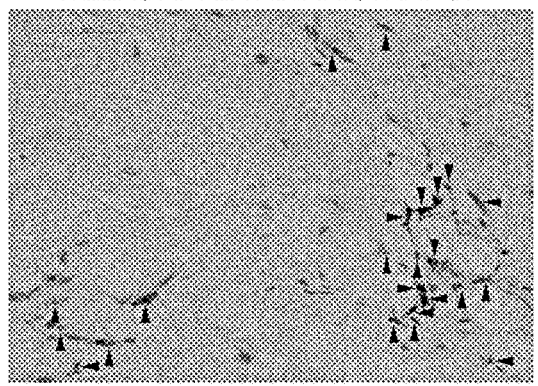
(23)

STEARIC ACID

PPARγ

ADMINISTRATION LOCATION FOUR WEEKS AFTER ADMINISTRATION (11)

ADMINISTRATION LOCATION EIGHT WEEKS AFTER ADMINISTRATION (15)

CD68

ADMINISTRATION LOCATION FOUR WEEKS AFTER ADMINISTRATION (13)

ADMINISTRATION LOCATION EIGHT WEEKS AFTER ADMINISTRATION (20)

MYRISTIC ACID

PPARγ

ADMINISTRATION LOCATION FOUR WEEKS AFTER ADMINISTRATION (14)

ADMINISTRATION LOCATION EIGHT WEEKS AFTER ADMINISTRATION (15)

CD68

ADMINISTRATION LOCATION FOUR WEEKS AFTER ADMINISTRATION (12)

ADMINISTRATION LOCATION EIGHT WEEKS AFTER ADMINISTRATION (26)

OLEIC ACID

P P A R γ

ADMINISTRATION LOCATION FOUR WEEKS AFTER ADMINISTRATION (7)

ADMINISTRATION LOCATION EIGHT WEEKS AFTER ADMINISTRATION (14)

C D 6 8

ADMINISTRATION LOCATION FOUR WEEKS AFTER ADMINISTRATION (6)

ADMINISTRATION LOCATION EIGHT WEEKS AFTER ADMINISTRATION (11)

α-LINOLENIC ACID

PPARγ

| ADMINISTRATION LOCATION FOUR WEEKS AFTER ADMINISTRATION | ADMINISTRATION LOCATION EIGHT WEEKS AFTER ADMINISTRATION |
|---|---|
|  |  |
| (7) | (13) |

CD68

| ADMINISTRATION LOCATION FOUR WEEKS AFTER ADMINISTRATION | ADMINISTRATION LOCATION EIGHT WEEKS AFTER ADMINISTRATION |
|---|---|
|  |  |
| (5) | (8) |

LINOLEIC ACID

PPARγ

ADMINISTRATION LOCATION FOUR WEEKS AFTER ADMINISTRATION (9)

ADMINISTRATION LOCATION EIGHT WEEKS AFTER ADMINISTRATION (10)

CD68

ADMINISTRATION LOCATION FOUR WEEKS AFTER ADMINISTRATION (4)

ADMINISTRATION LOCATION EIGHT WEEKS AFTER ADMINISTRATION (5)

FIG. 11A  LENGTH MEASUREMENT EXAMPLE (COMPARISON OF COURSE OF TREATMENT)
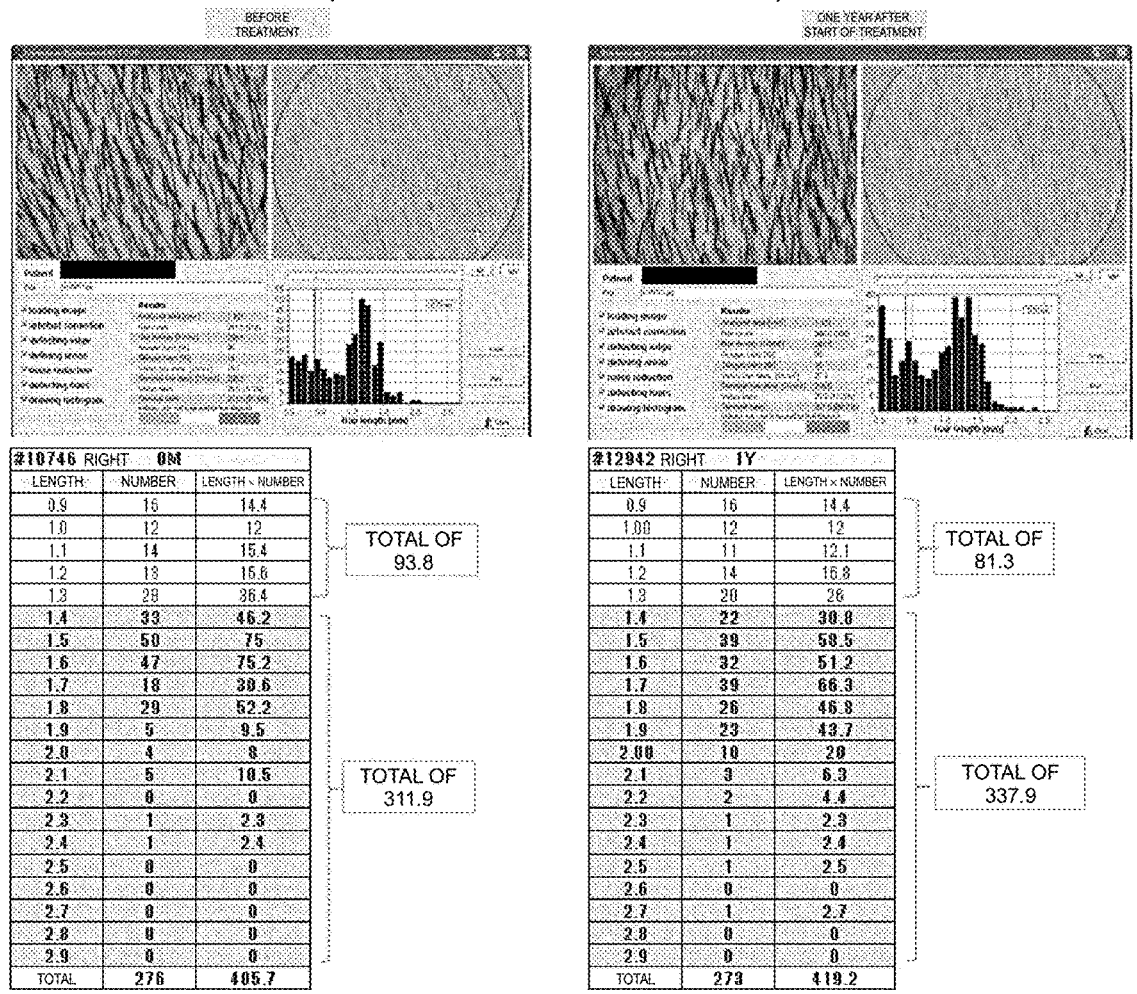
FIG. 11B
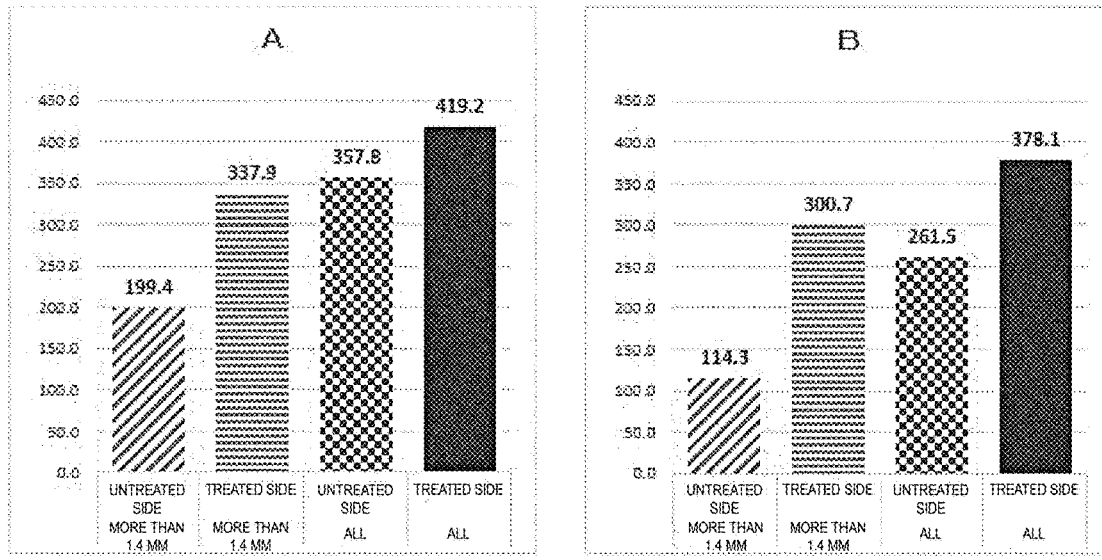

12 WEEKS OF AGE

CONTROL

PALMITIC ACID

THIN FILM

COLLECT TISSUES HAVING DIAMETER OF 3 MM AS BONE TISSUE SPECIMENS AFTER OSTEOGENESIS

COATED WITH PALMITIC ACID

CONTROL (ONLY THIN FILM)

| PIXEL VALUE | 1,549 |
| --- | --- |
| | 5,500 |
| | 768 |
| | 3,473 |
| | 842 |
| TOTAL | 12,132 |
| MEASURED VALUE (mm2) | 0.984 |

| PIXEL VALUE | 530 |
| --- | --- |
| | 495 |
| TOTAL | 1,025 |
| MEASURED VALUE (mm2) | 0.083 |

12 WEEKS OF AGE

SEQUENCE LISTING

<160> NUMBER OF SEQ ID NOS: 21

<210> SEQ ID NO 1
<211> LENGTH: 22
<212> TYPE: DNA
<213> ORGANISM: Artificial Sequence
<220> FEATURE:
<223> OTHER INFORMATION: Rp1P0 probe

```
<400> SEQUENCE: 1
cctgtcttcc ctgggcatca cg                                      22

<210> SEQ ID NO 2
<211> LENGTH: 17
<212> TYPE: DNA
<213> ORGANISM: Artificial Sequence
<220> FEATURE:
<223> OTHER INFORMATION: RplP0 forward primer

<400> SEQUENCE: 2
caatccctga cgcaccg                                            17

<210> SEQ ID NO 3
<211> LENGTH: 20
<212> TYPE: DNA
<213> ORGANISM: Artificial Sequence
<220> FEATURE:
<223> OTHER INFORMATION: RplP0 reverse primer

<400> SEQUENCE: 3
tgtctgctcc cacaatgaag                                         20

<210> SEQ ID NO 4
<211> LENGTH: 25
<212> TYPE: DNA
<213> ORGANISM: Artificial Sequence
<220> FEATURE:
<223> OTHER INFORMATION: Cxcl 12 probe

<400> SEQUENCE: 4
tcaacactcc aaactgtgcc cttca                                   25

<210> SEQ ID NO 5
<211> LENGTH: 20
<212> TYPE: DNA
<213> ORGANISM: Artificial Sequence
<220> FEATURE:
<223> OTHER INFORMATION: Cxcl 12 forward primer

<400> SEQUENCE: 5
gagccaacgt caaacatctg                                         20

<210> SEQ ID NO 6
<211> LENGTH: 21
<212> TYPE: DNA
<213> ORGANISM: Artificial Sequence
<220> FEATURE:
<223> OTHER INFORMATION: Cxcl12 reverse primer

<400> SEQUENCE: 6
ggctttgtcc aggtactctt g                                       21

<210> SEQ ID NO 7
<211> LENGTH: 25
<212> TYPE: DNA
<213> ORGANISM: Artificial Sequence
<220> FEATURE:
<223> OTHER INFORMATION: Cxcr4 probe

<400> SEQUENCE: 7
tcaacactcc aaactgtgcc cttca                                   25

<210> SEQ ID NO 8
<211> LENGTH: 18
```

```
<212> TYPE: DNA
<213> ORGANISM: Artificial Sequence
<220> FEATURE:
<223> OTHER INFORMATION: Cxcr4 forward primer

<400> SEQUENCE: 8
cgtttggtgc tccggtag                                          18

<210> SEQ ID NO 9
<211> LENGTH: 21
<212> TYPE: DNA
<213> ORGANISM: Artificial Sequence
<220> FEATURE:
<223> OTHER INFORMATION: Cxcr4 reverse primer

<400> SEQUENCE: 9
tctccagacc ctacttcttc g                                      21

<210> SEQ ID NO 10
<211> LENGTH: 25
<212> TYPE: DNA
<213> ORGANISM: Artificial Sequence
<220> FEATURE:
<223> OTHER INFORMATION: Itga4 probe

<400> SEQUENCE: 10
cgaaggacgt caaatcagcc agtca                                  25

<210> SEQ ID NO 11
<211> LENGTH: 23
<212> TYPE: DNA
<213> ORGANISM: Artificial Sequence
<220> FEATURE:
<223> OTHER INFORMATION: Itga4 forward primer

<400> SEQUENCE: 11
gcatctcctc tacatactca cag                                    23

<210> SEQ ID NO 12
<211> LENGTH: 20
<212> TYPE: DNA
<213> ORGANISM: Artificial Sequence
<220> FEATURE:
<223> OTHER INFORMATION: Itga4 reverse primer

<400> SEQUENCE: 12
caccaaccgc tacatcaaca                                        20

<210> SEQ ID NO 13
<211> LENGTH: 24
<212> TYPE: DNA
<213> ORGANISM: Artificial Sequence
<220> FEATURE:
<223> OTHER INFORMATION: Cd34 probe

<400> SEQUENCE: 13
tccctggaag taccagccac tact                                   24

<210> SEQ ID NO 14
<211> LENGTH: 23
<212> TYPE: DNA
<213> ORGANISM: Artificial Sequence
<220> FEATURE:
<223> OTHER INFORMATION: Cd34 forward primer

<400> SEQUENCE: 14
```

```
ggagtatttc caccagttcc tac                                          23

<210> SEQ ID NO 15
<211> LENGTH: 21
<212> TYPE: DNA
<213> ORGANISM: Artificial Sequence
<220> FEATURE:
<223> OTHER INFORMATION: Cd34 reverse primer

<400> SEQUENCE: 15
gatggctggt gtggtcttat t                                            21

<210> SEQ ID NO 16
<211> LENGTH: 30
<212> TYPE: DNA
<213> ORGANISM: Artificial Sequence
<220> FEATURE:
<223> OTHER INFORMATION: BMP4 probe

<400> SEQUENCE: 16
ccttgttttc tgtcaagaca ccatgattcc                                   30

<210> SEQ ID NO 17
<211> LENGTH: 22
<212> TYPE: DNA
<213> ORGANISM: Artificial Sequence
<220> FEATURE:
<223> OTHER INFORMATION: BMP4 forward primer

<400> SEQUENCE: 17
ataaaacgac catcagcatt cg                                           22

<210> SEQ ID NO 18
<211> LENGTH: 21
<212> TYPE: DNA
<213> ORGANISM: Artificial Sequence
<220> FEATURE:
<223> OTHER INFORMATION: BMP4 reverse primer

<400> SEQUENCE: 18
gcctttccag caagtttgtt c                                            21

<210> SEQ ID NO 19
<211> LENGTH: 22
<212> TYPE: DNA
<213> ORGANISM: Artificial Sequence
<220> FEATURE:
<223> OTHER INFORMATION: BMP7 probe

<400> SEQUENCE: 19
tgcgatgatc cagtcctgcc ag                                           22

<210> SEQ ID NO 20
<211> LENGTH: 22
<212> TYPE: DNA
<213> ORGANISM: Artificial Sequence
<220> FEATURE:
<223> OTHER INFORMATION: BMP7 forward primer

<400> SEQUENCE: 20
cgttcatgta ggagttcaga gg                                           22

<210> SEQ ID NO 21
<211> LENGTH: 22
<212> TYPE: DNA
<213> ORGANISM: Artificial Sequence
```

```
<220> FEATURE:
<223> OTHER INFORMATION: BMP7 reverse primer

<400> SEQUENCE: 21
ctgtatgtta gcttccgaga cc                                              22
```

PHARMACEUTICAL COMPOSITION FOR USE IN INCREASING HAIR, MODIFYING SCALP OR SKIN, HEALING A WOUND, PROMOTING OSTEOGENESIS, OR MODIFYING HAIR

CROSS-REFERENCE TO RELATED APPLICATIONS

This application is a continuation of U.S. patent application Ser. No. 16/635,221, which is the National Stage of PCT/JP2018/047736, filed on Dec. 26, 2018, and claims priority to Japanese Application No. 2017-249980, filed on Dec. 26, 2017, the disclosures of all of which are incorporated herein by reference in their entireties.

TECHNICAL FIELD

The present invention relates to a pharmaceutical composition for use in increasing hair, modifying scalp or skin, healing wounds, promoting osteogenesis, or modifying hair; and a method.

BACKGROUND ART

Mammalian milk (particularly colostrum) contains various substances including nutrients, such as immune substances, intracellular transmitters, exosomes, mRNA and cytokines. When an infant orally ingests the milk, these substances are taken into the body to contribute to growth of the infant.

Fat-lineage cells have been reported to drive hair cycling by contributing to niches of skin stem cells in comparative studies with and without fat lineage cells (Non Patent Literature 1). Non Patent Literature 1 indicates that emergence of CD34 positive cells, increase in the number of PPAR-γ-positive fat cells and maturity of fat cells are related to growth of growing hair. Non Patent Literature 2 reports that the number of tissue-resident M2-like macrophages increases in the occurrence of tissue regeneration in tissues.

CITATION LIST

Non Patent Literature

Non Patent Literature 1: Festa E et al., Cell, 146: 761-71, 2011
Non Patent Literature 2: Satoh T. et al, Nature, 495: 524-528, 2013

SUMMARY OF INVENTION

The present invention provides a pharmaceutical composition for topical administration for use in modifying scalp or skin. The present invention also provides a pharmaceutical composition for topical administration for use in treating a wound. The present invention further provides a pharmaceutical composition for topical administration for use in promoting hair increase or modifying hair.

The present inventors have found that milk, supernatant ingredients of centrifugated milk and soybean oil, and compositions containing fatty acids such as main fatty acids contained therein are useful for modifying scalp or skin, healing wounds, promoting osteogenesis, and modifying hair. The present invention is based on these findings.

The following invention will be provided according to the present invention.

(1) A pharmaceutical composition comprising a therapeutically effective amount of a saturated fatty acid or a pharmaceutically acceptable salt thereof, the pharmaceutical composition being (i) a pharmaceutical composition for topical administration for use in modifying scalp or skin, (ii) a pharmaceutical composition for topical administration for use in treating a wound, or (iii) a pharmaceutical composition for topical administration for use in promoting hair increase or a pharmaceutical composition for topical administration for use in modifying hair.

(2) The pharmaceutical composition according to (1) above, for use in modifying scalp or skin.

(3) The pharmaceutical composition according to (1) above, for use in treating a wound.

(4) The pharmaceutical composition according to (1) above, for use in promoting hair increase.

(5) The pharmaceutical composition according to (1) above, for use in promoting osteogenesis.

(6) The pharmaceutical composition according to (6) above, wherein the saturated fatty acid is in a form applied to a biocompatible film.

(7) The pharmaceutical composition described in any one of (1) to (6) above, wherein the saturated fatty acid is one or more fatty acids selected from the group consisting of palmitic acid, stearic acid and myristic acid.

(8) The pharmaceutical composition described in any one of (1) to (7) above, further comprising an unsaturated fatty acid.

(9) The pharmaceutical composition described in any one of (1) to (6) above, comprising soybean oil or milk or an extracted product or a processed product thereof which contains a therapeutically effective amount of a saturated fatty acid or a pharmaceutically acceptable salt thereof.

(10) The pharmaceutical composition according to (9) above, wherein the milk is sterilized.

(11) The pharmaceutical composition according to (10) above, wherein the milk is sterilized at a high temperature.

The present invention is advantageous in that it provides a pharmaceutical composition or a treatment method which can be used for various pharmaceutical applications as described above and which is capable of continuously exhibiting an effect even after completion of treatment.

BRIEF DESCRIPTION OF DRAWINGS

FIG. 10B shows the results of staining of CD68 and PPAR-γ-positive cells in tissues four weeks and eight weeks after administration of palmitic acid. The arrowheads in the Figure, each indicate a location at which positive cells are present, and the number in parentheses in the lower right of each stained image indicates the number of positive cells in the visual field.

FIG. 11A shows the sum of values each obtained by multiplying the length by the number of hairs for each hair length after administration of milk.

FIG. 11B is a form of a bar graph showing the results of FIG. 11A. In the FIG. 11B, the "1.4 mm or more" means the sum of the lengths of hairs that are 1.4 mm or more in length, and the "all" means the sum of the lengths of hairs having a length of 0.9 mm or more.

DESCRIPTION OF EMBODIMENTS

Figure 1:
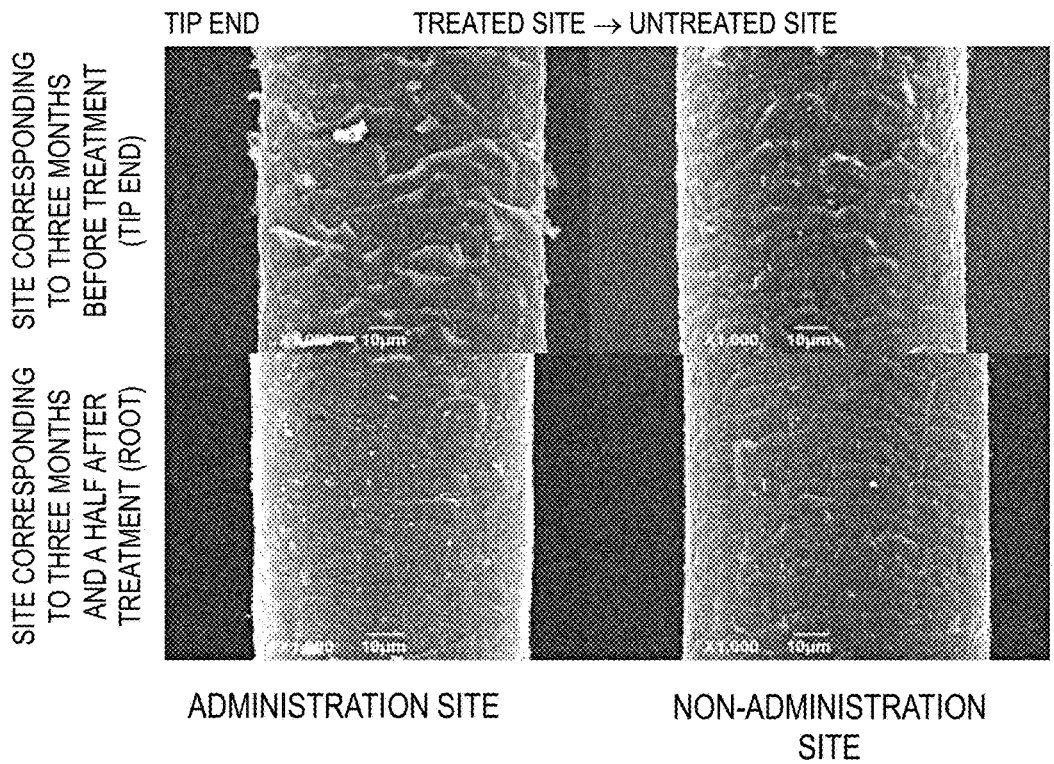
FIG. 1 is a photograph showing an influence of administration of milk on cuticles of hair.

As used herein, the "subject" means a mammal. Examples of the mammal include humans (males and females).

As used herein, the "milk" means mammal-derived milk. Examples of the mammal include humans and bovines.

As used herein, the "milk serum" means an aqueous solution obtained by removing milkfat components and casein from milk. The milk serum can be obtained by, for example, subjecting milk to treatment such as centrifugation and removing precipitates.

As used herein, the "scalp" means the skin of a region of the head, which is inclusive of the top of the head but exclusive of the face, the jaw and the neck (including ears). As used herein, the "skin" is construed as including the scalp and the skin other than the scalp. The scalp of a human has an area of about 700 $mm^2$ to about 800 $mm^2$.

As used herein, the "modification" means that the quality is improved, ameliorated, upgraded or made better. As used herein, the "improvement" is construed as including betterment of a current situation and betterment of bad portions.

As used herein, the "hair" means hair growing on the skin. As used herein, the "head hair" means hair growing on the scalp.

As used herein, the "white hair" means hair, particularly head hair, which exhibits a white color due to the lack of pigments such as eumelanin (or true melanin) and/or pheomelanin. As used herein, the "black hair" means hair containing eumelanin and exhibiting a black color.

As used herein, the "cuticle" is a structure covering the surface of hair and existing on the outermost layer of the hair. The cuticle has a role in protecting hair against external stimuli and a role in preventing loss of moisture or ingredients to the outside from the internal cortex. The cuticle covers hair in a scalelike manner by extending from the root to the tip end of the hair.

As used herein, the "wound" means physical damage to tissues. The wound includes wounds of the body surface.

The present invention provides:

(A) a pharmaceutical composition for topical administration for use in modifying scalp or skin, the pharmaceutical composition containing a therapeutically effective amount of a fatty acid (particularly a saturated fatty acid) or a pharmaceutically acceptable salt thereof;

(B) a pharmaceutical composition for topical administration for use in treating a wound, the pharmaceutical composition containing a therapeutically effective amount of a fatty acid (particularly a saturated fatty acid) or a pharmaceutically acceptable salt thereof;

(C) a pharmaceutical composition for topical administration for use in promoting hair increase, or a pharmaceutical composition for topical administration for use in modifying hair, the pharmaceutical composition containing a therapeutically effective amount of a fatty acid (particularly a saturated fatty acid) or a pharmaceutically acceptable salt thereof; and (D) a pharmaceutical composition for use in promoting osteogenesis, the pharmaceutical composition containing a therapeutically effective amount of a fatty acid (particularly a saturated fatty acid) or a pharmaceutically acceptable salt thereof (hereinafter, the pharmaceutical compositions according to (A) to (D) above are sometimes referred to collectively as a "pharmaceutical composition of the present invention").

In certain embodiments of the present invention, examples of the composition containing a therapeutically effective amount of a saturated fatty acid or a pharmaceutically acceptable salt thereof include milk, milk extracted products (e.g. milk serum) and milk processed products (e.g. dairy products, e.g. cheese milk serum and yogurt milk serum), and mixtures thereof. The milk, milk extracted products or milk processed products may be sterilized, for example sterilized at a low temperature (e.g. sterilized by heating at 62° C. to 68° C.) or sterilized at a high temperature (sterilized by heating at 120° C. or higher). Sterilization of milk is normally classified broadly into low-temperature sterilization performed at 62° C. to 68° C. for about 30 minutes (e.g. at 65° C. for 30 minutes) and high-temperature sterilization performed at 120° C. to 150° C. for 1 second to 4 seconds (e.g. 120° C. to 130° C. for 2 seconds to 3 seconds). Therefore, in certain embodiments of the present invention, the pharmaceutical composition of the present invention contains milk as an active ingredient.

In certain embodiments of the present invention, examples of the composition containing a therapeutically effective amount of a saturated fatty acid or a pharmaceutically acceptable salt thereof include animal oil, vegetable oil, extracted products or processed products of these oils (e.g. soybean oil, soybean oil extracted products or soybean oil processed products), and mixtures thereof.

As used herein, the extracted product from milk or soybean oil is a fraction extracted from milk or soybean, may be called a milk extracted product or a soybean oil extracted product, and contains a therapeutically effective amount of a saturated fatty acid or a pharmaceutically acceptable salt thereof.

As used herein, the processed product of milk or soybean oil is a product obtained by processing milk or soybean oil, may be called a milk processed product or a soybean processed product, and contains a therapeutically effective amount of a saturated fatty acid or a pharmaceutically acceptable salt thereof.

Examples of the composition containing a therapeutically effective amount of a saturated fatty acid or a pharmaceutically acceptable salt thereof include solutions containing milk and milk serum, and freeze-dried preparations thereof.

The fatty acid contained in the pharmaceutical composition for topical administration according to the present invention may be a fatty acid contained as an ingredient of milk.

In certain embodiments of the present invention, the saturated fatty acid contained in the pharmaceutical composition for topical administration according to the present invention is one or more saturated fatty acids selected from the group consisting of palmitic acid, stearic acid and myristic acid.

In certain embodiments of the present invention, the fatty acid contained in the pharmaceutical composition for topical administration according to the present invention may be a saturated fatty acid, and is one or more fatty acids selected from the group consisting of palmitic acid, stearic acid and myristic acid.

In certain embodiments of the present invention, the saturated fatty acid contained in the pharmaceutical composition for topical administration according to the present invention is palmitic acid.

In certain embodiments of the present invention, the saturated fatty acid contained in the pharmaceutical composition for topical administration according to the present invention is stearic acid.

In certain embodiments of the present invention, the saturated fatty acid contained in the pharmaceutical composition for topical administration according to the present invention is myristic acid.

In certain embodiments of the present invention, the pharmaceutical composition for topical administration according to the present invention may further contain an unsaturated fatty acid, and the unsaturated fatty acid may be, for example, one or more unsaturated fatty acids selected from the group consisting of oleic acid, α-linolenic acid and linoleic acid.

In certain embodiments of the present invention, the fatty acid contained in the pharmaceutical composition for topical administration according to the present invention is oleic acid.

The fatty acid contained in the pharmaceutical composition for topical administration according to the present invention is α-linolenic acid.

The fatty acid contained in the pharmaceutical composition for topical administration according to the present invention is linoleic acid.

In certain embodiments, the fatty acid contained in the pharmaceutical composition for topical administration according to the present invention may be a mixture of at least one saturated fatty acid and at least one unsaturated fatty acid. In certain embodiments, the pharmaceutical composition for topical administration according to the present invention contains palmitic acid and linoleic acid as the fatty acid. In certain embodiments, the pharmaceutical composition for topical administration according to the present invention contains palmitic acid and oleic acid as the fatty acid. In certain embodiments, the pharmaceutical composition for topical administration according to the present invention contains stearic acid and linoleic acid as the fatty acid. In certain embodiments, the pharmaceutical composition for topical administration according to the present invention contains stearic acid and oleic acid as the fatty acid. In certain embodiments, the pharmaceutical composition for topical administration according to the present invention contains palmitic acid, stearic acid and linoleic acid as the fatty acid. In certain embodiments, the pharmaceutical composition for topical administration according to the present invention contains palmitic acid, stearic acid and oleic acid as the fatty acid. In certain embodiments, the pharmaceutical composition for topical administration according to the present invention contains myristic acid, palmitic acid, stearic acid, oleic acid, linoleic acid and α-linolenic acid as the fatty acid.

In certain embodiments, milk, a milk extracted product, a milk processed product or a mixture thereof, which can be used in the present invention, may contain one or more fatty acids selected from saturated fatty acids {here, the phrase "may contain fatty acids" include cases where the milk naturally contains the fatty acids and cases where the fatty acids are added to the milk}. In certain embodiments, milk, a milk extracted product, a milk processed product or a mixture thereof, which can be used in the present invention, may further contain an unsaturated fatty acid. In certain embodiments, milk, a milk extracted product, a milk processed product or a mixture thereof, which can be used in the present invention, may contain, for example, one or more fatty acids selected from the group consisting of palmitic acid, stearic acid and myristic acid. In certain embodiments, milk, a milk extracted product, a milk processed product or a mixture thereof, which can be used in the present invention, may contain, for example, one or more unsaturated fatty acids selected from the group consisting of oleic acid, α-linolenic acid and linoleic acid. In certain embodiments, milk, a milk extracted product, a milk processed product or a mixture thereof, which can be used in the present invention, may contain, for example, one or more saturated fatty acids and one or more unsaturated fatty acids. In certain embodiments, milk, a milk extracted product, a milk processed product or a mixture thereof, which can be used in the present invention, may contain one or more fatty acids selected from the group consisting of palmitic acid, stearic acid and myristic acid and one or more fatty acids selected from the group consisting of oleic acid, α-linolenic acid and linoleic acid. In certain embodiments, milk, a milk extracted product, a milk processed product or a mixture thereof, which can be used in the present invention, may contain myristic acid, palmitic acid and oleic acid. In certain embodiments, milk, a milk extracted product, a milk processed product or a mixture thereof, which can be used in the present invention, may contain myristic acid, palmitic acid, stearic acid, oleic acid, linoleic acid and α-linolenic acid. In certain embodiments of the present invention, the one or more fatty acids can be added to the pharmaceutical composition in the form of milk, a milk extracted product, a milk processed product or a mixture thereof.

In certain embodiments of the present invention, milk, a milk extracted product, a milk processed product or a mixture thereof may have an increased content of one or more fatty acids selected from saturated fatty acids and unsaturated fatty acids. The increase of the content means that the content of the fatty acids in milk, a milk extracted product, a milk processed product or a mixture thereof is higher after the increase of the content than before the increase of the content. The increase of the content can be performed by, for example, adding one or more fatty acids selected from saturated fatty acids and unsaturated fatty acids to milk, a milk extracted product, a milk processed product or a mixture thereof. In certain embodiments, the increase of the content may be, for example, the increase of the content of one or more fatty acids selected from the group consisting of palmitic acid, stearic acid and myristic acid. In certain embodiments, the increase of the content may be, for example, the increase of the content of one or more fatty acids selected from the group consisting of oleic acid, α-linolenic acid and linoleic acid. In certain embodiments, the increase of the content may be the increase of the content of one or more saturated fatty acids and one or more unsaturated fatty acids. In certain embodiments, the increase of the content may be, for example, the increase of the content of one or more fatty acids selected from the group consisting of palmitic acid, stearic acid and myristic acid and the content of one or more fatty acids selected from the group consisting of oleic acid, α-linolenic acid and linoleic acid. In certain embodiments, the increase of the content may be the increase of the content of each of myristic acid, palmitic acid and oleic acid. In certain embodiments, the increase of the content may be the increase of the content of each of myristic acid, palmitic acid, stearic acid, oleic acid, linoleic acid and α-linolenic acid.

In certain embodiments of the present invention, milk, a milk extracted product, a milk processed product or a mixture thereof may have a reduced lactoferrin content. The lactoferrin content may be reduced by a method such as high-temperature sterilization.

Milk, a milk extracted product, a milk processed product or a mixture thereof may have an increased fatty acid content and a reduced lactoferrin content.

In certain embodiments of the present invention, animal oil, vegetable oil, an extracted product or a processed product of the oil or a mixture thereof may contain one or more fatty acids selected from saturated fatty acids. In certain embodiments, animal oil, vegetable oil, an extracted product or a processed product of the oil or a mixture thereof may further contain an unsaturated fatty acid. In certain embodiments, animal oil, vegetable oil, an extracted product or a processed product of the oil or a mixture thereof, which can be used in the present invention, may contain, for example, one or more fatty acids selected from the group consisting of palmitic acid, stearic acid and myristic acid. In certain embodiments, animal oil, vegetable oil, an extracted product or a processed product of the oil or a mixture thereof, which can be used in the present invention, may contain, for example, one or more unsaturated fatty acids selected from the group consisting of oleic acid, α-linolenic acid and linoleic acid. In certain embodiments, animal oil, vegetable oil, an extracted product or a processed product of the oil or a mixture thereof, which can be used in the present invention, may contain, for example, one or more saturated fatty acids and one or more unsaturated fatty acids. In certain embodiments, animal oil, vegetable oil, an extracted product or a processed product of the oil or a mixture thereof, which can be used in the present invention, may contain one or more fatty acids selected from the group consisting of palmitic acid, stearic acid and myristic acid and one or more fatty acids selected from the group consisting of oleic acid, α-linolenic acid and linoleic acid. In certain embodiments, animal oil, vegetable oil, an extracted product or a processed product of the oil or a mixture thereof, which can be used in the present invention, may contain myristic acid, palmitic acid and oleic acid. In certain embodiments, animal oil, vegetable oil, an extracted product or a processed product of the oil or a mixture thereof, which can be used in the present invention, may contain myristic acid, palmitic acid, stearic acid, oleic acid, linoleic acid and α-linolenic acid.

In certain embodiments of the present invention, animal oil, vegetable oil, an extracted product or a processed product of the oil or a mixture thereof may have an increased content of one or more fatty acids selected from saturated fatty acids and unsaturated fatty acids. The increase of the content means that the content of the fatty acids in animal oil, vegetable oil, an extracted product or a processed product of the oil or a mixture thereof is higher after the increase of the content than before the increase of the content. The increase of the content can be performed by, for example, adding one or more fatty acids selected from saturated fatty acids and unsaturated fatty acids to animal oil, vegetable oil, an extracted product or a processed product of the oil or a mixture thereof. In certain embodiments, the increase of the content may be, for example, the increase of the content of one or more fatty acids selected from the group consisting of palmitic acid, stearic acid and myristic acid. In certain embodiments, the increase of the content may be, for example, the increase of the content of one or more fatty acids selected from the group consisting of oleic acid, α-linolenic acid and linoleic acid. In certain embodiments, the increase of the content may be the increase of the content of one or more saturated fatty acids and one or more unsaturated fatty acids. In certain embodiments, the increase of the content may be, for example, the increase of the content of one or more fatty acids selected from the group consisting of palmitic acid, stearic acid and myristic acid and the content of one or more fatty acids selected from the group consisting of oleic acid, α-linolenic acid and linoleic acid. In certain embodiments, the increase of the content may be the increase of the content of each of myristic acid, palmitic acid and oleic acid. In certain embodiments, the increase of the content may be the increase of the content of each of myristic acid, palmitic acid, stearic acid, oleic acid, linoleic acid and α-linolenic acid.

In certain embodiments, the pharmaceutical composition for topical administration according to the present invention contains the fatty acid in a soluble form. In certain embodiments, the pharmaceutical composition for topical administration according to the present invention contains the fatty acid as a pharmaceutically acceptable salt. In certain embodiments, the pharmaceutical composition for topical administration according to the present invention contains the fatty acid in an emulsion form. In certain embodiments, the fatty acid is not in either an ester form or a glyceride form in the pharmaceutical composition for topical administration according to the present invention.

The fatty acid is soluble in dimethyl sulfoxide, ethanol, chloroform and diethyl ether. The water solubility of the fatty acid is improved when the fatty acid is in the form of a pharmaceutically acceptable salt, for example a sodium salt. The fatty acid salt may be dissolved in water by forming micelles.

In certain embodiments, the pharmaceutical composition for topical administration according to the present invention may be a preparation for injection. In certain embodiments of the present invention, the pharmaceutical composition for topical administration according to the present invention may be provided in the form of a kit including a freeze-dried preparation of a fatty acid-containing solution and water for injection, and the freeze-dried preparation may be prepared with the water for injection at the time of need. The water for injection may be heated before use.

The pharmaceutical composition for use in promoting osteogenesis according to the present invention may be provided in a state of being applied to a biocompatible film. Therefore, the present invention can provide a pharmaceutical agent containing a therapeutically effective amount of a saturated fatty acid applied onto a biocompatible film, or a pharmaceutically acceptable salt thereof. Examples of the biocompatible film include thin films having a surface of calcium phosphate (e.g. thin films of calcium phosphate), thin films having a surface of polylactic acid (e.g. thin films of polylactic acid), thin films having a surface of polyglycolic acid (e.g. thin films of polyglycolic acid), thin films of a surface of a copolymer or block copolymer of lactic acid and polyglycolic acid (e.g. thin films of a copolymer or block copolymer of lactic acid and polyglycolic acid) and thin films having a surface of hydroxyapatite (e.g. thin films of hydroxyapatite). The application of an active ingredient onto the biocompatible film can be performed by, for example, adding dropwise a solution of the active ingredient onto the biocompatible film, and drying the added solution. For example, about 10 to 50 μg of the pharmaceutical active ingredient can be applied to the biocompatible film.

The pharmaceutical composition for topical administration containing a therapeutically effective amount of a saturated fatty acid or a pharmaceutically acceptable salt thereof, for use in modifying scalp or skin, improves the scalp from the vicinity of an administration portion after administration, and the effect is gradually propagated to the surroundings with time. Therefore, the composition can be scattered on the scalp or skin to propagate the effect of the present invention to the surroundings with time, or densified to reduce the time required for propagation. In certain embodiments of the present invention, the administration density of the pharmaceutical composition of the present invention is not particularly limited, and may be 1 location per 1 $cm^2$ to 10 $cm^2$, 1 $cm^2$ to 5 $cm^2$, 1 $cm^2$ to 4 $cm^2$, 1 $cm^2$ to 3 $cm^2$, 1 $cm^2$ to 2 $cm^2$, 0.5 $cm^2$ to 2 $cm^2$ or 0.7 $cm^2$ to 1.5 $cm^2$. In certain embodiments of the present invention, the pharmaceutical composition of the present invention can be administered at an administration density of, for example, 1 or less location per 0.5 $cm^2$, 1 or less location per 0.6 $cm^2$, 1 or less location per 0.7 $cm^2$, 1 or less location per 0.8 $cm^2$, 1 or less location per 0.9 $cm^2$, or 1 or less per 1 $cm^2$. In certain embodiments of the present invention, for example, the pharmaceutical composition of the present invention can be topically administered immediately under the skin or over the dermis layer to the upper fat layer. The administration can be performed by, for example, injection.

A therapeutically effective amount of the saturated fatty acid or a pharmaceutically acceptable salt thereof can be administered in the form of a solution in an amount of, for example, 10 μL to 50 μL, 15 μL to 30 μL, 15 μL to 25 μL or about 20 μL per location.

The administration site can be appropriately selected, and for example, the composition can be administered to the entire scalp, or administered to a poorer portion as compared to other portions of the entire scalp.

Surprisingly, the present inventors have found that when the composition is administered to a relatively good site of the entire scalp, the effect thereof is easily propagated. The good portion has high responsiveness to the pharmaceutical composition of the present invention, and the effect is propagated to the surroundings of the administration location. The improvement effect through propagation is more remarkable at a location closer to the administration location, and covers a range of several cm (e.g. 1 cm to 4 cm) from the administration location. Therefore, the composition can be administered to a relatively good site of the scalp. Since the improvement effect is propagated from the good site to the relatively poor site, a therapeutic effect on the poor site can be obtained by administrating the composition only to the relatively good site.

Therefore, the composition may be administered to a relatively good site of the scalp to improve a poorer portion through the propagation effect. When improvement is attained at a relatively poor site, responsiveness to the pharmaceutical composition of the present invention is enhanced. Therefore, the composition may be administered to a relatively good site of the scalp to advance improvement of a poorer portion through the propagation effect, followed by administering the pharmaceutical composition of the present invention to the portion that was poor.

It is considered that every time the pharmaceutical composition of the present invention is administered, tissue stimuli, the activity of macrophage and the activity of immature fat cells are raised to enhance the repair function at the administration site. It is desirable to administer the composition in light of the symptom (condition) of a patient and the degree of improvement.

In certain embodiments, the topical administration can be applied to 150 locations to 250 locations (e.g. about 200 locations) or 250 locations to 800 locations per adult scalp, and the number of administration locations can be determined as necessary. Here, the term "about" means inclusion of a numerical value range within ±10% or ±5% from the numerical value following this term.

The administration interval of the pharmaceutical composition of the present invention is not particularly limited, and for example, the pharmaceutical composition can be administered at an interval of once a month to once per 6 months, twice a month to once per 5 months, twice a month to once per 4 months, twice a month to once per 3 months, twice a month to once per 2 months, 1.5 times a month to once per 1.5 months, or 1.2 times a month to once per 1.2 months, for example about once a month.

The pharmaceutical composition of the present invention exhibits a scalp or skin modification effect even when administered only once, and this effect can be sustained. Therefore, the administration may be performed once, or two or more times. The pharmaceutical composition of the present invention can be continuously administered until treatment is completed or until a patient is satisfied. Particularly, according to the present invention, the scalp or skin modification effect is exhibited earlier at a portion having a good condition than at a portion having a bad condition. Therefore, the treatment period and the treatment interval may vary depending on the condition of the scalp or skin. The treatment period with the pharmaceutical composition of the present invention may be, for example, one treatment at the shortest to 3 years, one treatment at the shortest to 2 years, one treatment at the shortest to 1.5 years, one treatment at the shortest to 1 year, one treatment at the shortest to eight months, one treatment at the shortest to six months, or one treatment at the shortest to four months. The pharmaceutical composition of the present invention may be administered before, when or after an age-related change is observed in the hair, scalp or skin. Administration of the pharmaceutical composition of the present invention may be started again before, when or after an age-related change is observed in the hair, scalp or skin of a subject after treatment with the pharmaceutical composition.

In certain embodiments of the present invention, the pharmaceutical composition according to (A) above may be a pharmaceutical composition for rejuvenation or promotion of rejuvenation of the scalp or skin. In certain embodiments of the present invention, the pharmaceutical composition according to (A) above may be a pharmaceutical composition for regeneration or promotion of regeneration of the scalp or skin. In certain embodiments of the present invention, the pharmaceutical composition according to (A) above may be a pharmaceutical composition for activation of the scalp or skin. In certain embodiments of the present invention, the pharmaceutical composition according to (A) above can be used in combination with a hair increasing agent or a hair growing agent.

In certain embodiments of the present invention, the pharmaceutical composition according to (B) above can be used for treating a wound. In the present invention, the treatment of a wound may be healing of a wound, promotion of healing of a wound or acceleration of healing of a wound.

Improvement of the scalp induces an effect on the hair itself. As shown in Examples below, examples of the hair improvement effect include reduction of white hair, reduction of the weight of white hair portions, reduction of the ratio of white hairs, improvement of roughness of cuticles, and improvement of the thickness and the growth rate of hair. Therefore, in certain embodiments of the present invention, the pharmaceutical composition according to (C) above may be a pharmaceutical composition for use in reducing white hair. Examples of the reduction of white hair include reduction of the number of white hairs, reduction of the weight of white hair portions and reduction of the ratio of white hairs. Reduction of white hair may be associated with increase in the number of hairs colored with various kinds of melanin, increase in the weight of such hair portions and increase in the ratio of such hairs. In certain embodiments of the present invention, the pharmaceutical composition according to (C) above may be a pharmaceutical composition for use in improving roughness of cuticles of hair. Examples of the improvement of roughness of cuticles of hair include enhancement of the alignment level of cuticles, and reduction of the area of regions where cuticles are disordered. In certain embodiments of the present invention, the pharmaceutical composition according to (C) above may be a pharmaceutical composition for use in improving the thickness or the growth rate of hair. Examples of the improvement of the thickness of hair include thickening of hair, increasing of the number of thick hairs, and increasing of the ratio of thick hairs. Examples of the improvement of the growth rate include increasing of the number or the ratio of hairs having an growth rate of 10 mm or more, 11 mm or more, 12 mm or more, 13 mm or more, 14 mm or more, 15 mm or more, 16 mm or more, 17 mm or more, 18 mm or more, 19 mm or more, 20 mm or more or 21 mm or more a month.

In certain aspects, the present invention provides:

(a) a method for modifying scalp or skin in a subject in need thereof (in a site in need thereof), the method including topically administering a therapeutically effective amount of a saturated fatty acid or a pharmaceutically acceptable salt thereof to the scalp or skin;

(b) a method for treating a wound in a subject in need thereof, the method including topically administering a therapeutically effective amount of a saturated fatty acid or a pharmaceutically acceptable salt thereof to the scalp or skin;

(c) a method for promoting hair increase in a subject in need thereof or modifying hair in a subject in need thereof, the method including topically administering a therapeutically effective amount of a saturated fatty acid or a pharmaceutically acceptable salt thereof to the scalp or skin; and (d) a method for promoting osteogenesis in a subject in need thereof, the method including topically administering a therapeutically effective amount of a fatty acid (particularly a saturated fatty acid) or a pharmaceutically acceptable salt thereof to a site in need of osteogenesis (e.g. damaged site of bone) (here, a therapeutically effective amount of a fatty acid (particularly a saturated fatty acid) or a pharmaceutically acceptable salt thereof may be administered in a state of being applied to a biocompatible film).

In certain aspects, the present invention provides:

(α) use of a therapeutically effective amount of a saturated fatty acid or a pharmaceutically acceptable salt thereof in manufacture of a pharmaceutical formulation for topical administration for use in modifying scalp or skin;

(β) use of a therapeutically effective amount of a saturated fatty acid or a pharmaceutically acceptable salt thereof in manufacture of a pharmaceutical formulation for topical administration for use in treating a wound;

(γ) use of a therapeutically effective amount of a saturated fatty acid or a pharmaceutically acceptable salt thereof in manufacture of a pharmaceutical formulation for topical administration for use in promoting hair increase or modifying hair; and (δ) use of a therapeutically effective amount of a saturated fatty acid or a pharmaceutically acceptable salt thereof in manufacture of a pharmaceutical composition or a pharmaceutical formulation for use in promoting osteogenesis (here, a therapeutically effective amount of a fatty acid (particularly a saturated fatty acid) or a pharmaceutically acceptable salt thereof in the pharmaceutical preparation can be provided in a state of being applied to a biocompatible film).

In certain embodiments of the present invention, the pharmaceutical composition may contain excipients (e.g. solvents, co-solvents, solubilizers, wetting agents, suspensions, thickeners, emulsifiers, chelating agents, buffers, buffer solutions, pH adjusters, antioxidants, reducing agents, antibacterial agents, preservatives, fillers, protective agents and/or isotonic agents) in addition to a therapeutically effective amount of a fatty acid or a pharmaceutically acceptable salt thereof. In certain embodiments of the present invention, the pharmaceutical composition may be in the form of an injection. In certain embodiments of the present invention, the pharmaceutical composition may be topically administered, for example intracutaneously or subcutaneously administered.

EXAMPLES

Example 1: Preparation and Administration of Milk (1) Milk was Prepared in the Following Manner.

As milk to be administered to humans, so-called colostrum (milk collected within three weeks after delivery) was obtained from 34-year-old and 40-year-old females using a milk pump.

As milk to be administered to rats, bovine colostrum obtained by hand milking or commercially available bovine milk was used as bovine milk.

(2) Milk was Administered in the Following Manner.

Milk was injected in an amount of 20 μL per location into the right half or the left half of a human scalp or a dorsal skin of a rat. For the humans, 2 mL of colostrum in total was injected into one patient on a half of the head of the patient (i.e. 100 locations per patient). For the rats, three regions were defined between the head and the tail of the dorsal part of a 12-week-old Wistar rat (male), and each region was divided between the left and the right of the backbone into two regions to set a total of six regions on the dorsal part. Milk was injected in an amount of 20 μL per location at two locations in the vicinity of the center of each region. The distance between the two locations was 1 cm.

Example 2: Change in Hair Quality

In this Example, improvement of cuticles of hair before and after treatment was examined.

The human colostrum described in Example 1 was used as milk. The average growth rate of hair is about 10 mm per month. One hair was collected from each of an administration site and a non-administration site, and with consideration given to the growth rate of hair of the patient, a hair portion corresponding to three months before treatment and a hair portion corresponding to three and a half months after the start of treatment were each taken as a sample. On the hair collection day or the next day, hair of the examination site was firmly bonded to a fixation plate with resin. On the next day or the day after next, the hair was subjected to carbon fixation, and on the same day, the state of cuticles of hair was observed with a scanning electron microscope by a conventional method. As a negative control, an untreated portion (non-administration site) of the same patient was used. A newly grown portion (root side) and an existing portion (tip end side) were compared to each other. FIG. 1 shows a representative example. FIG. 1 shows an electron microscope image of hair of the same patient.

The results showed that for the treated hair, cuticles were rough on the tip end side, whereas cuticles were orderly on the root side where hair was newly grown portion, and thus the hair quality difference was evidently improved. On the other hand, for the hair of the untreated portion as a negative control, cuticles were rough on the root side and the tip end side, and there was no hair quality improvement effect in the untreated portion.

The same evaluation was performed on a larger number of patients. The evaluation was performed in accordance with the following scores based on electron microscope images. Seven healthcare professionals including doctors etc. performed the evaluation. An average value of scores was calculated.

Score Table for Hair Quality Evaluation

Score 5: Cuticles are orderly, and are not rough.

Score 4: Cuticles are more orderly than the average, and are slightly rough.

Score 3: Cuticles are as orderly as the average.

Score 2: Cuticles are rougher than the average, and are slightly peeled.

Score 1: Cuticles are generally rough, and are generally peeled.

Table 1 shows the results.

TABLE 1

| Improvement in hair quality evaluation by treatment | | | |
|---|---|---|---|
| Patient No. | Score (root on the treated side) | Score (root on the untreated side) | Score (tip end on the treated side) |
| 1 | 4.43 | 2.86 | 3.29 |
| 1 | 3.71 | 3.00 | 2.00 |
| 2 | 3.29 | 3.86 | 3.00 |
| 2 | 3.29 | 2.29 | 3.29 |
| 3 | 3.43 | 3.29 | 3.00 |
| 3 | 3.43 | 2.71 | 3.14 |
| 4 | 3.43 | 3.29 | 2.57 |
| 4 | 3.14 | 2.14 | 2.00 |
| Total average | 3.52 | 2.93 | 2.79 |

As shown in Table 1, a difference between the scores of the tip end and the root of the same hair, and the results showed that the root had a higher score on both the treated side and the untreated side. Specifically, the average score for the electron microscope images of roots on the treated side were 3.52, whereas the average score for tip ends on the treated side was 2.79, and the difference between these average scores was statistically significant (p=0.017). More specifically, the improvement degree (score of root−score of tip end) was 0.73 on the treated side and 0.39 on the untreated side, and thus the improvement degree was higher on the treated side (n=4, 33 to 56 years of age, four females, average age of 45.8). As shown in Table 1, the average score for roots on the treated side was 3.52, whereas the average score for roots on the untreated side was 2.93, and thus the difference between the scores for roots on the treated side and the untreated side was confirmed to be statistically significant (p=0.036). This revealed that due to administration of milk, a hair quality improvement effect was exhibited on a root portion on the treated side, i.e. a hair portion newly produced after treatment.

Example 3: Change in Hair Quality

In this Example, attention was given to the hair color (white hair), and the hair color improvement effect was examined before and after treatment.

Specifically, the tails of both eyes of the patient were extended, two points at which the extended tails crossed lines connecting both ears and the top of the head were tattooed with India ink, and hair was shaved within a circle with a radius of 2 cm around the marking. Three days after shaving hair, 2 mL of the human colostrum described in Example 1 was injected into the scalp on a half of the head. Here, the human colostrum was injected at 100 locations in an amount of 20 µL per location. The scalp was observed after a month. A trichogram was taken with the marking set at the center every time (Canon Power Shot A520, Tokyo, Japan), hair within a circle falling within the photographed range and having a diameter of 11 mm (an area of 95 mm$^2$) with the tattoo at the center was photographed, and the amount of hair was visually measured.

The results showed that with respect to the hair-shaven part, all of three patients having white hair before treatment had reduced white hair six months after single-injection treatment, and white hair was reduced by 7.7 hairs/95 mm$^2$ in the above photographed range (n=3). The number of white hairs was reduced to 92.9% before and after treatment on the treated side. Where the number of white hairs before the start of treatment on the untreated side is defined as 100, the white hair reduction ratio on the untreated side was lower by 28.2% than that on the treated side when the number of white hairs before the start of treatment on the treated side is defined as 100, and this shows that white hair was greatly reduced on the treated side (n=3).

Figure 2A:
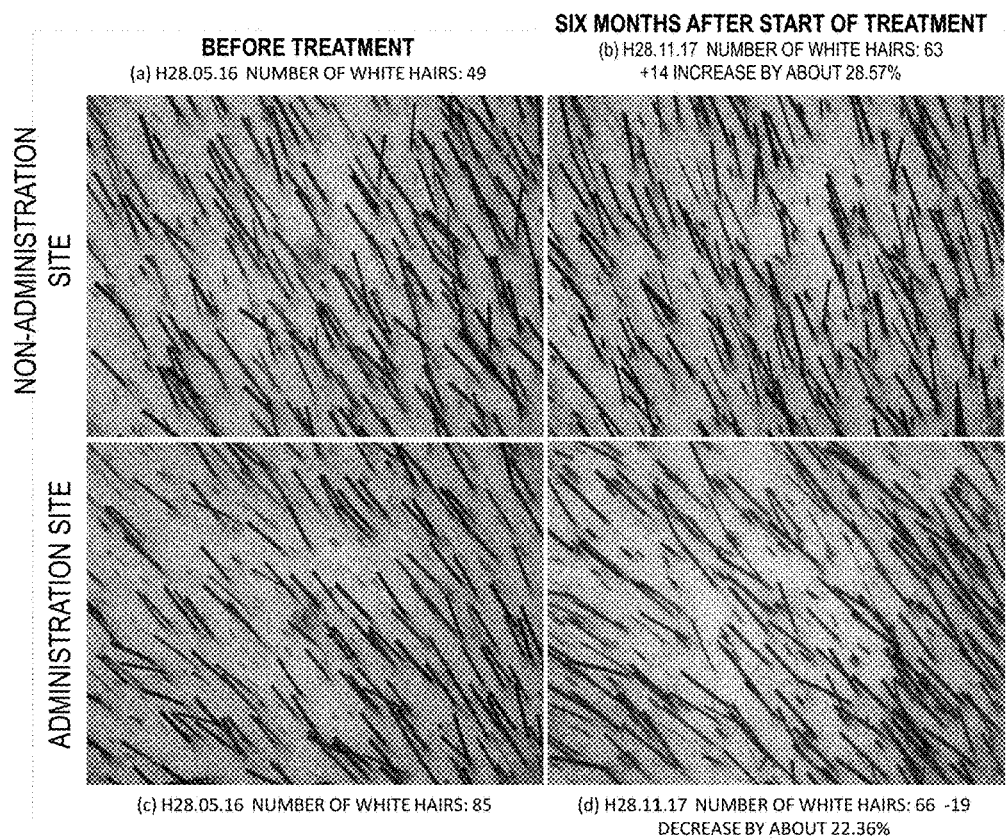
FIG. 2A is photographs of a topical area which shows an effect of administration of milk on reduction of white hair.

FIG. 2A shows a representative example of head hair of a patient (48-year-old female) after passage of half year after shaving of hair and single injection of colostrum. As shown in FIG. 2A, white hair was not reduced in the non-administration site, and white hair was evidently reduced in the administration site. Specifically, in the non-administration site, the number of white hairs was 49 before treatment, and increased to 63 after six months, whereas in the administration site, the number of white hairs was 85 before treatment, and decreased to 66 after treatment.

Figure 2B:
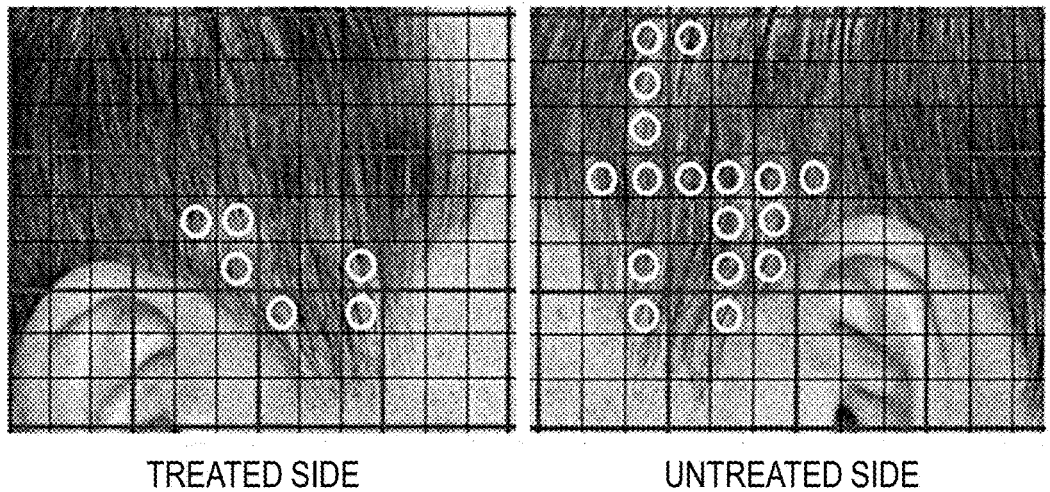
FIG. 2B is photographs of a lateral surface of the head which shows an effect of administration of milk on reduction of white hair.

Further, for a patient (50-year-old male) in whom the human colostrum described in Example 1 had been injected into the scalp four times in an amount of 20 µL per location, the side of the head thirteen months after the start of treatment was compared to the side of the head on the untreated side. FIG. 2B shows the results. As shown in FIG. 2B, the area of white hair regions was 833 cm$^2$ in the side of the head on the untreated side, whereas the area of white hair was 294 cm$^2$ in the side of the head on the treated side. Thus, it was revealed that administration of colostrum reduced white hair. In FIG. 2B, a grid was superimposed on a photograph of the side of the head, and among cells of the grid, cells determined to be white by visual inspection was given a symbol "0". On the treated side, the number of symbols "0" was evidently smaller as compared to the untreated side.

Example 4: Verification of Scalp Modification Effect

Modification of the scalp, based on which hair was modified as described above, was verified.

As milk, the human colostrum described in Examples was used. Milk was injected into the scalp of the patient at 100 locations in an amount of 20 µL per location (six patients were injected once, and one patient was injected four times at an interval of once a month).

Figure 3:
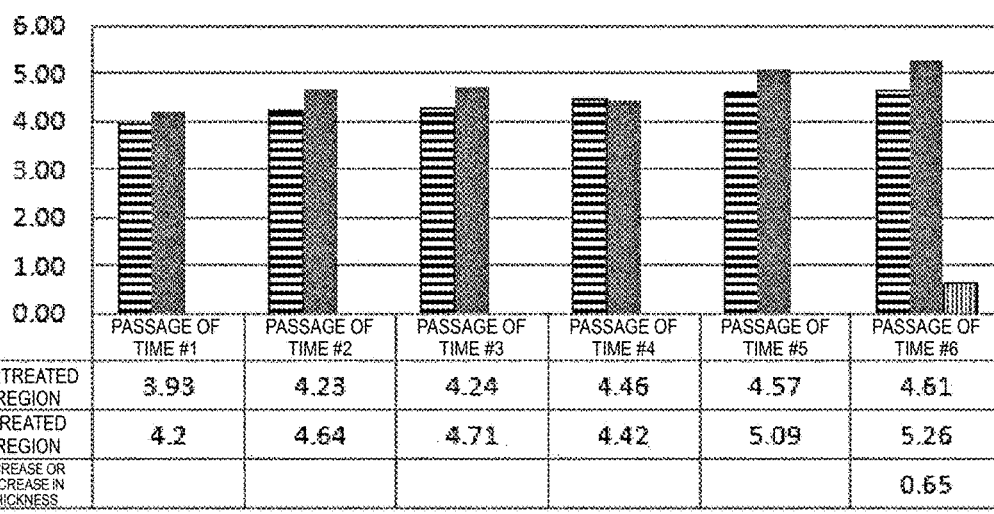
FIG. 3 shows a relationship between administration of milk and the thickness of a fat layer of the skin, where symbols #1 to #6 denote, respectively, one to six months after treatment.

In echo examination using a probe at 10 Mz, a change in thickness of the fat layer of subcutaneous tissues of the scalp after single administration was observed. In this examination, it is considered that the region of a lower portion from the sebaceous gland region is measured as the thickness of a region approximately to the dermis layer (the measured value does not include the dermis layer). FIG. 3 shows the results. In FIG. 3, symbols "#1" to "#6" indicate that data is obtained one to six months, respectively, after treatment. As shown in FIG. 3, the thickness of the fat layer slightly increased but did not greatly change six months after the start of treatment.

Example 5: Scalp Tissue Image

In Examples above, a cuticle improvement effect and a white hair reduction effect were confirmed. In this Example, the amount of collagen in the scalp was examined for determining whether these effects stemmed from improvement of the scalp.

Milk was subcutaneously administered into the scalp of a human patient in an amount of 20 µL per location. The administration was performed once per month. As the milk, the human colostrum described in Example 1 was used.

(1) Change in Collagen Image

First, an increase or decrease in amounts of type I collagen and type III collagen was observed.

Specifically, a section of a scalp tissue (surface extending toward the skull bone from the epidermis) was prepared, and using Picrosirius Red Stain Kit reagent (Polysciences, Inc., Cat #: 24901-250), type I collagen and type III collagen were stained in accordance with written instructions from the manufacturer. Type I collagen was stained yellow, and type III collagen was stained green. In this system, collagen other than type III collagen was stained reddish yellow.

Figure 4A:
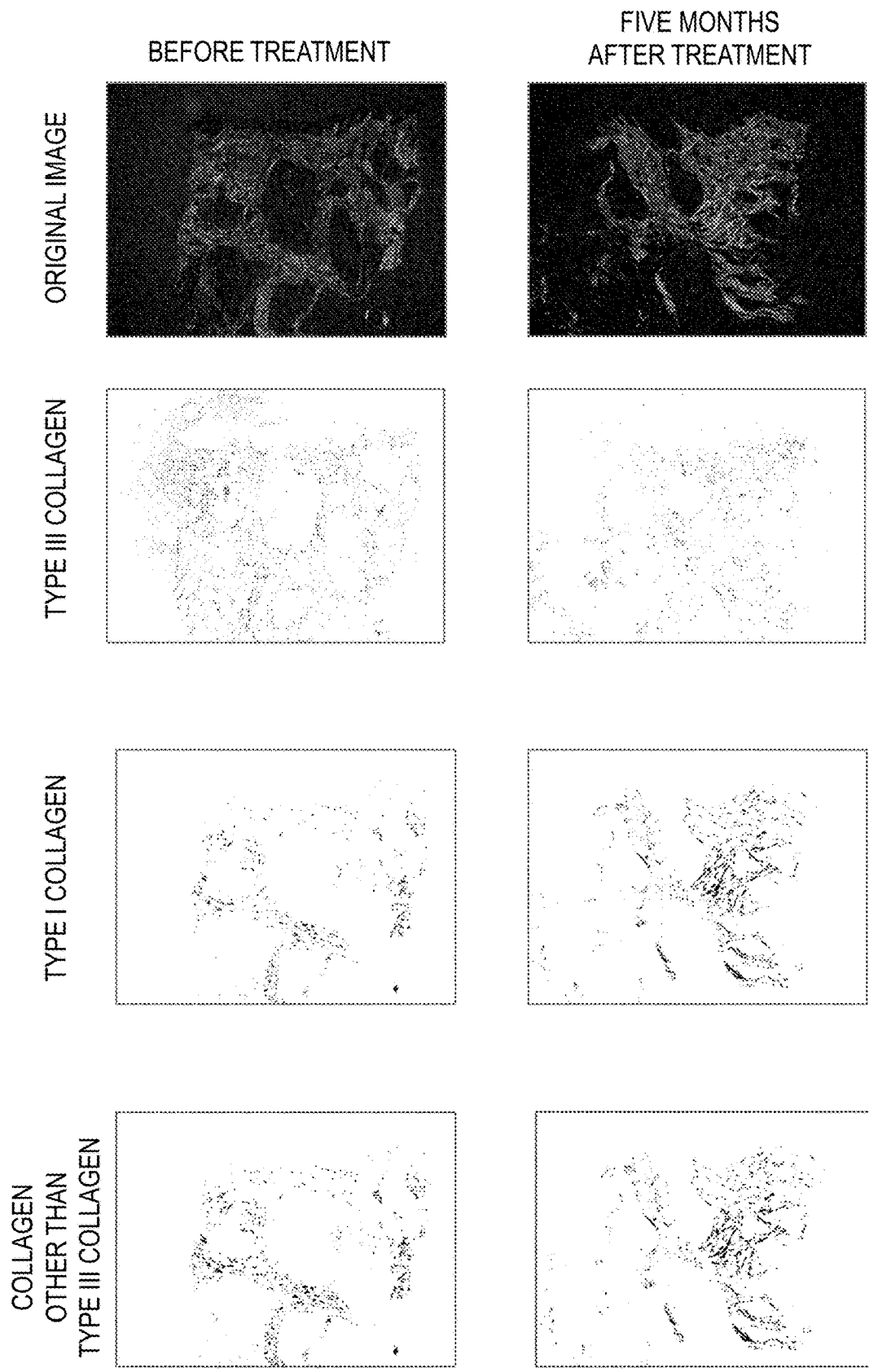
FIG. 4A shows stained tissues of type I collagen and type III collagen in skin tissues before and after treatment.

The stained images were observed with a microscope (Nikon Corporation or Olympus Corporation) equipped with a polarizing filter device, and were photographed with a camera (DP-22 from Olympus Corporation or DS-Fi3 from Nikon Instech Co., Ltd.) accompanying the microscope. The images were stored in a computer as digital images in a gray scale, and the amount of collagen was estimated from the intensities of pixels. FIG. 4A shows a scalp sample from a female patient (49 years of age) after passage of five months after single administration, and FIG. 4B shows a male patient (50 years of age) after passage of fifteen months after initial treatment, with administration performed four times at an interval of once a month.

Figure 4B:
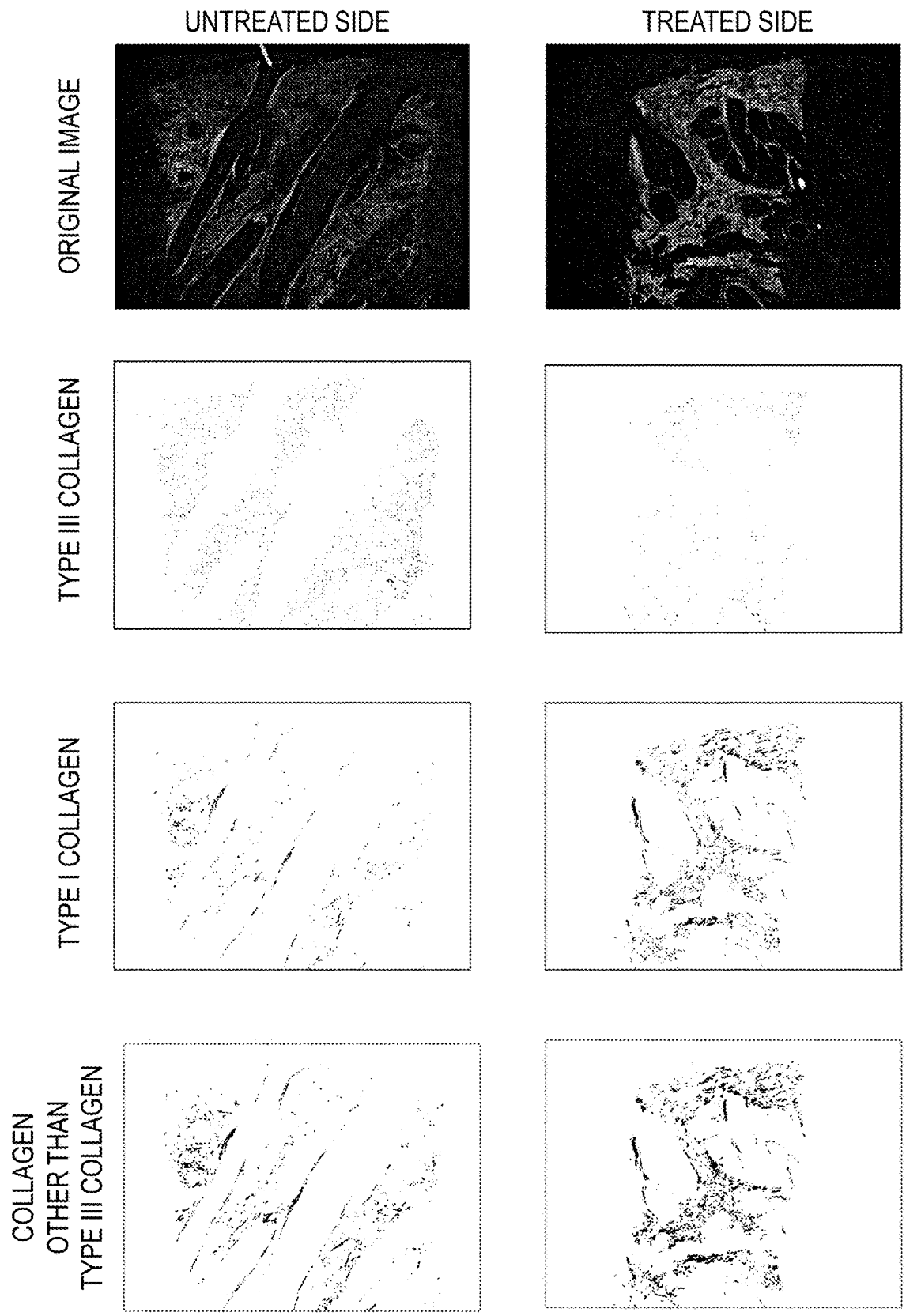
FIG. 4B shows stained tissues of type I collagen and type III collagen in skin tissues before and after treatment.

The results showed that type I collagen and type III collagen were present before treatment and on the untreated side as shown in FIGS. 4A and 4B.

The number of green pixels (corresponding to the amount of type III collagen), the number of yellow pixels (corresponding to the amount of type I collagen) and the number of reddish-yellow pixels (corresponding to the total amount of collagen other than type III collagen) in FIG. 4A are collectively shown in a table.

TABLE 2

Results of analysis of pixels in photographs of FIG. 4A

| Number of pixels | Before treatment | After treatment | Increase or decrease (percentage point difference) |
|---|---|---|---|
| Green | 27,084 (49.6%) | 11,217 (19.6%) | Decrease of 30.0 percentage points |
| Reddish yellow | 27,546 (50.4%) | 46,022 (80.4%) | Increase of 30.0 percentage points |
| Number of yellow pixels included | 16,469 (30.1%) | 35,635 (62.3%) | Increase of 32.1 percentage points |
| Total | 54,630 (100%) | 57,239 (100%) | |

*The number indicates the number of pixels in the photograph, and the number in parentheses indicates a ratio thereof to the total number of pixels.

As shown in Table 2, it is apparent that in the patient after passage of five months after single administration, the ratio of type III collagen decreased from 49.6% to 19.6%, and the ratio of type I collagen increased from 30.1% to 62.3%. It is apparent that the total amount of all collagen other than type III collagen similarly increased from 50.4% to 80.4%, and this increase may result mainly from increase in the amount of type I collagen.

The number of green pixels (corresponding to the amount of type III collagen), the number of yellow pixels (corresponding to the amount of type I collagen) and the number of reddish-yellow pixels (corresponding to the total amount of collagen other than type III collagen) in FIG. 4B are collectively shown in a table.

TABLE 3

Results of analysis of pixels in photographs of FIG. 4B

| Number of pixels | Untreated side | Treated side | Increase or decrease (percentage point difference) |
|---|---|---|---|
| Green | 9,640 (26.3%) | 1,815 (2.8%) | Decrease of 23.5 percentage points |
| Reddish yellow | 27,023 (73.7%) | 62,214 (97.2%) | Increase of 23.5 percentage points |
| Number of yellow pixels included | 9,047 (24.7%) | 36,071 (56.3%) | Increase of 31.7 percentage points |
| Total | 36,663 (100%) | 64,029 (100%) | |

*The number indicates the number of pixels in the photograph, and the number in parentheses indicates a ratio thereof to the total number of pixels.

As shown in Table 3, it is found that in the patient fifteen months after the start of treatment, the ratio of type III collagen greatly decreased from 26.3% to 2.8% and the ratio of type I collagen increased from 24.7% to 56.3% on the treated side as compared to the untreated side (see FIG. 4B). It is apparent that the total amount of all collagen other than type III collagen similarly increased from 73.7% to 97.2%, and this increase may result mainly from increase in the amount of type I collagen.

The same tendency was exhibited in both before-and-after comparison on the treated side and left-and-right comparison between the untreated side and the treated side, and it was revealed that administration of milk decreased the amount of type III collagen and increased the amount of type I collagen. Further, a similar observation was made on human specimens (n=3), and the results showed that for all the specimens, administration of milk decreased the amount of type III collagen, and increased the amount of type I collagen. These results showed that the amount of collagen stained reddish yellow (collagen other than type III collagen) increased similarly to the amount of type I collagen stained yellow.

A phenomenon in which the amount of type III collagen decreases and the amount of type I collagen increases occurs in repair of tissues, particularly in wound healing. The results in this Example indicate that administration of milk induces repair of tissues in the scalp and skin.

(2) Rejuvenation of Fat Cells

Then, rejuvenation of fat cells was observed.

Figure 5:
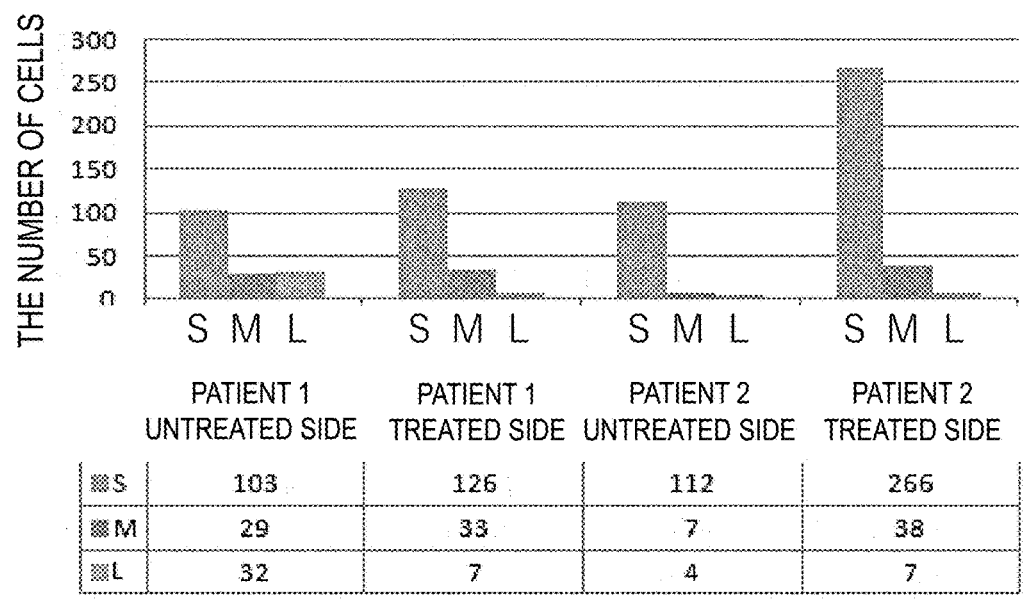
FIG. 5 shows an effect of administration of milk on the size of fat cells.

As a fat cell grows, most of the cytoplasm turns into fat droplets, so that fat droplet is accumulated in the cytoplasm, leading to enlargement of the cell. Thus, a large cell means a matured old cell, and a small cell is considered to be an immature new cell (i.e. immature fat cell). In this Example, whether administration of milk increased the number of small immature cells was examined. More specifically, a human scalp tissue section given 20 μL of milk was observed to examine a change in size of fat cells in the fat layer. Images of fat cells were taken as approximate circles, and the cells were classified as S, M or L. Cells with the diameter of 51 μm or less were defined as "S", cells with the diameter of more than 51 μm and 63 μm or less were defined as "M", and cells with the diameter of more than 63 μm were defined as "L". The cells of each class were counted. The patients employed are as follows: a patient six months after single administration (hereinafter, referred to as "patient 1"); and a patient fifteen months after the start of treatment with administration performed four times at an interval of once a month (hereinafter, referred to as "patient 2"). FIG. 5 shows the results.

As shown in FIG. 5, administration of milk remarkably increased the ratio of fat cells "S" in both the patient six months after treatment (patient 1, 51-year-old male) and the patient fifteen months after treatment (patient 2, 50-year-old male). Comparison between patient 1 and patient 2 showed that the ratio of fat cells "S" increased more remarkably in patient 2. This revealed that the four-time treatment increased the ratio of fat cells "S" more greatly than the one-time treatment.

These results show that administration of milk increases the number of immature cells, leading to rejuvenation of tissues. In addition, it is indicated that rejuvenation of tissues may lead to enhancement of the tissue repair ability.

Example 6: Effect on Wound Healing

In this Example, whether or not administration of milk had an effect of accelerating healing of wounds on the skin was examined.

Formation of wounds: hair on the dorsal part of a 12-week-old Wistar rat was shaven with hair clippers, and a circular full-thickness skin defect with a diameter of 8 mm was produced on each of the left and right sides of the head and the left and right sides of the tail. The full-thickness skin defect was formed at four locations per body.

Administration of milk: 20 µL of milk was subcutaneously injected at each of four locations, namely upper, lower, left and right, in a place 4 mm away from the peripheral edge of the wound. As the milk, the commercially available bovine milk sterilized by heating (at 130 degrees for 2 seconds and 65 degrees for 30 minutes) as described in Example 1 was used.

Administration of fatty acid: As a fatty acid contained in the milk, sterile purified water (administration liquid) containing palmitic acid, stearic acid, myristic acid, linolenic acid, α-linoleic acid and oleic acid, respectively was administered. Here, the water was heated and administered for the saturated fatty acids, and the water was administered at room temperature for the unsaturated fatty acids. 20 µL of the administration liquid (containing 1 mg of the fatty acid) was subcutaneously administered at each of four locations, namely upper, lower, left and right, in a place 4 mm away from the peripheral edge of the wound.

Wound Healing Score

Score 5: Healed

Score 4: The reduction ratio of the area of the wound site is 70% or more.

Score 3: The reduction ratio of the area of the wound site is 50% or more and less than 70%.

Score 2: The reduction ratio of the area of the wound site is 20% or more and less than 50%.

Score 1: The reduction ratio of the area of the wound site is less than 20%.

Figure 6A:
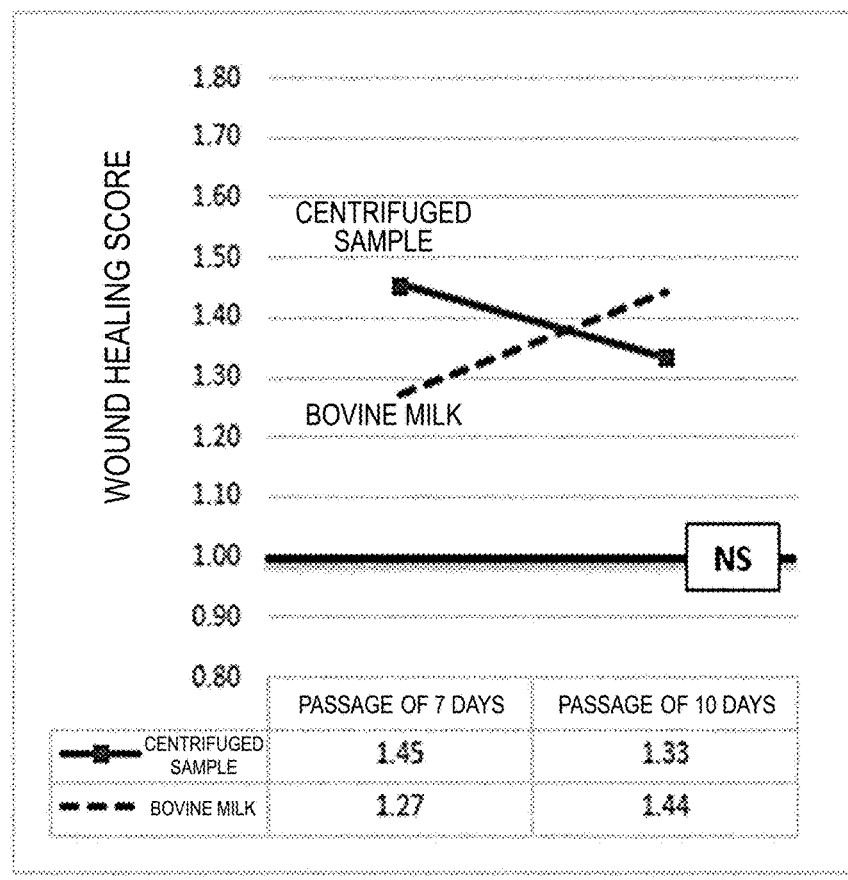
FIG. 6A shows an effect of administration of milk on wound healing.

The result was given as a ratio obtained by dividing the above score by the score for physiological saline. As shown in FIG. 6A, a wound healing-promoting effect was exhibited in a group given milk.

Two tubes of 8 mL of commercially available milk sterilized at a low temperature (65 degrees for 30 minutes) were centrifuged by a centrifugal separator (2600 g×6 minutes), 2 mL of one fourth of the supernatant exclusive of a whip portion was collected from each tube, the two collected liquids were combined to obtain 4 mL of a liquid, and 4 mL of the resulting liquid was stirred, and used for experiments (hereinafter, the obtained sample is referred to as a "centrifuged sample"). The obtained centrifuged sample was administered to the wound site at a dosage of 20 µL per location in the same manner as described above. The results are shown in "Centrifuged Sample" in FIG. 6A.

As shown in FIG. 6A, the centrifuged sample exhibited a wound healing improvement effect equivalent to or higher than that of milk. This indicated that the wound healing effect of milk was an effect of ingredients contained in a component that was not precipitated by centrifugation. It was shown that wounds were naturally healed after administration of physiological saline, and either administration of milk or administration of the centrifuged sample promoted healing as compared to natural healing after administration of physiological saline (FIG. 6A).

Figure 6B:
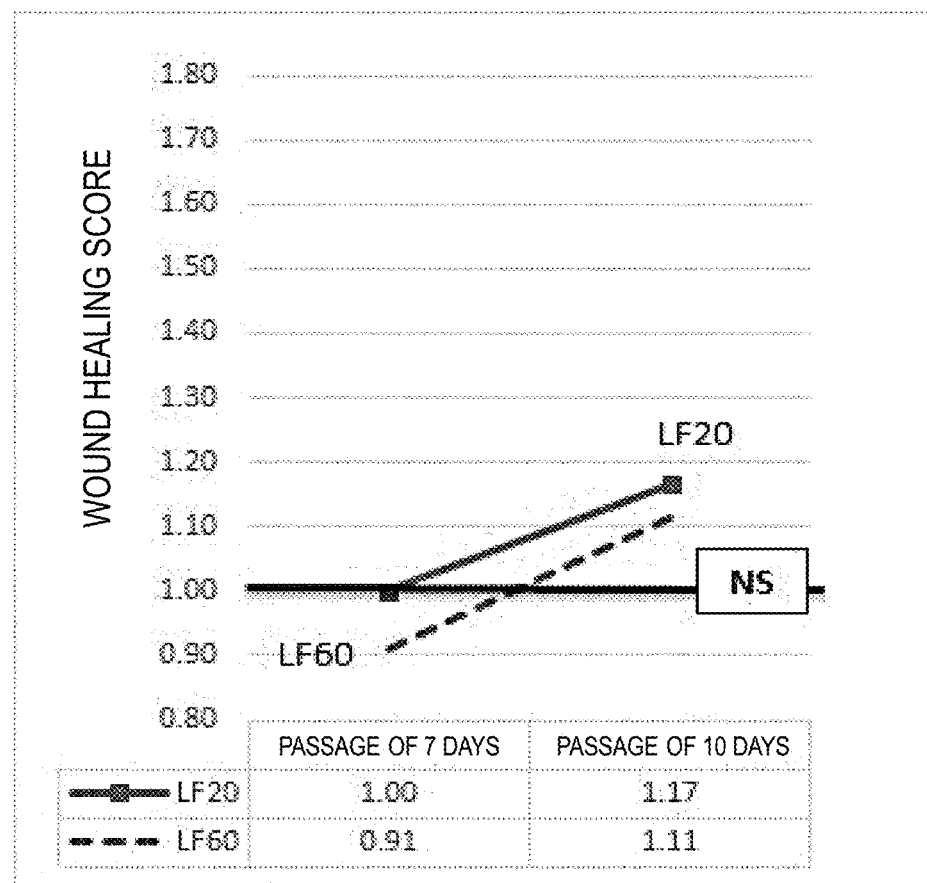
FIG. 6B shows an effect of administration of lactoferrin on wound healing.

Next, a wound healing-promoting effect of lactoferrin was examined. As lactoferrin, Nice rim essence 62971 (trade name) purchased from Lion Corporation was used and administered at one location in an amount of 20 µg or 60 µg in the same manner as described above. Specifically, the lactoferrin was ground, and then thoroughly dissolved in purified water. The lactoferrin concentration was adjusted so that an injection amount of 20 µL included the above administration amount. The result was given as a value obtained by dividing each of scores after seven days and after ten days by the score for the physiological saline administration group. FIG. 6B shows the results. As shown in FIG. 6B, the lactoferrin did not exhibit a significant promoting effect on wound healing. This showed that ingredients other than lactoferrin had a wound healing-promoting effect.

Normal raw milk is considered to contain lactoferrin (also referred to as "LF") in an amount of about 3 mg per L. Thus, 20 µL of raw milk contains about 0.06 µg of lactoferrin. Lactoferrin is sensitive to heat, and thus may be mostly eliminated from the bovine milk sterilized by heating at a high temperature and used in Examples above (see Mirai Noro, et al., "Electrophoresis" 59: 21-24, 2015). Therefore, the conclusion that lactoferrin is not an active ingredient is supported by the fact that a wound healing-promoting effect was exhibited in administration of bovine milk sterilized at a high temperature, and a wound healing-promoting effect was exhibited in administration of the centrifuged sample, whereas there was almost no wound healing-promoting effect in administration of lactoferrin.

Example above reveals that administration of milk or a centrifuged supernatant of milk promotes wound healing. Example above also indicates that administration of milk or a centrifuged supernatant of milk may vitalize regeneration of tissues of the skin.

Figure 6C:
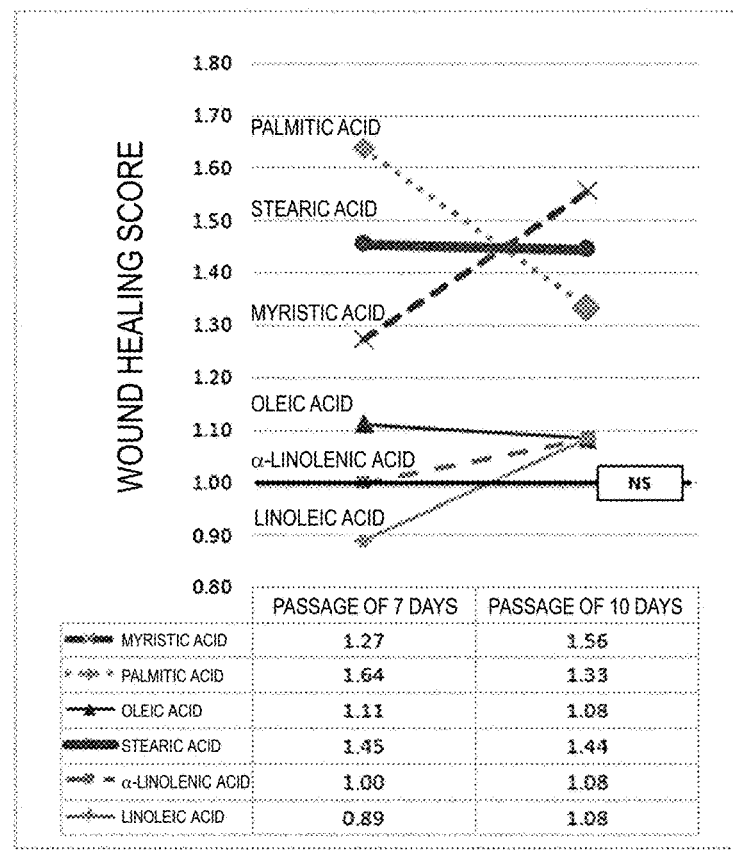
FIG. 6C shows an effect of administration of a saturated fatty acid or an unsaturated fatty acid on wound healing.

Next, active ingredients of milk were identified. Specifically, fatty acids contained in the milk were each administered to a wound part as described above, and whether a wound healing-promoting effect was exhibited or not was examined. FIG. 6C shows the results. As shown in FIG. 6C, palmitic acid, stearic acid and myristic acid were revealed to have a high promoting effect on wound healing. This revealed the possibility that these fatty acids contributed to the wound healing-promoting effect in administration of milk. Oleic acid, α-linolenic acid and linoleic acid had a weak wound healing-promoting effect.

Figure 6D:
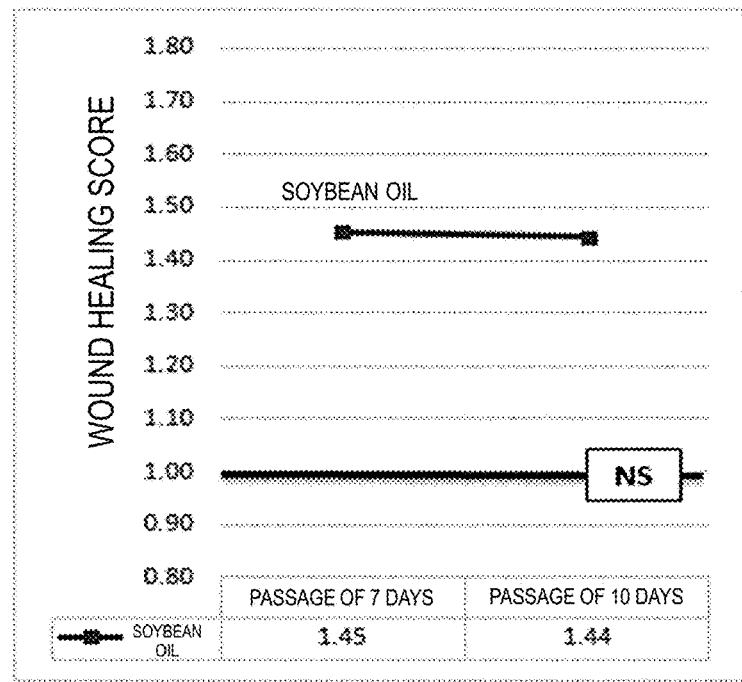
FIG. 6D shows an effect of administration of soybean oil on wound healing.

Edible soybean oil (manufactured by RIKEN Nosan-Kako Co., Ltd., Fukuoka Factory) known to be rich in palmitic acid, stearic acid, linoleic acid and α-linolenic acid was administered to a wound part, and whether a wound healing-promoting effect was exhibited or not was examined. FIG. 6D shows the results. As shown in FIG. 6D, the soybean oil exhibited a high promoting effect on wound healing.

Representative fatty acids contained in common bovine milk and soybean oil, and the contents thereof in 1 g of the bovine milk and 1 g of the soybean oil are shown below.

TABLE 4

Typical fatty acids contained in bovine milk and soybean oil, and content thereof (unit: mg/g of edible part)

| Fatty acid ingredient | Content (bovine milk) | Content (soybean oil) |
| --- | --- | --- |
| Myristic acid | 3.6 | 0.71 |
| Palmitic acid | 10 | 99 |
| Stearic acid | 4 | 40 |
| Oleic acid * | 7.6 | 220 |
| Linoleic acid | 0.88 | 500 |
| α-linolenic acid | 0.13 | 61 |

Standard Tables of Food Composition in Japan, 2015 (seventh revised edition), Fatty Acid Composition Section
Calculated from Table 1. Fatty Acid Composition per 100 g of Edible Part
* Oleic acid includes cis-vaccenic acid Example 7: Detection of Tissue-Resident M2-Like Macrophages and PPAR-γ-Positive Fat Cells in Scalp Tissues after Administration of Milk It has been reported that at the time when regeneration of tissues occurs in peripheral tissues (particularly fat tissues), the number of tissue-resident M2-like macrophages increases (Satoh T., et al., Nature, 495: 524-528, 2013), CD34-positive cells are produced, or the number of PPAR-γ-positive fat cells increases (Festa E, et al., Cell, 146: 761-71, 2011). Thus, in this Example, whether the number of tissue-resident M2-like macrophages increased or the number of PPAR-γ-positive cells increased in scalp tissues after administration of 20 μL of milk was examined. In addition, whether the number of Ki67-positive cells increased as an activation marker of cell growth in the 12-week-old Wistar rat dorsal skin was examined. The tissue-resident M2-like macrophages were detected as CD68-positive cells or CD163-positive cells. In this Example, as milk, human colostrum was administered to humans, and bovine colostrum was administered to rats.

A tissue section of the dorsal skin of each rat in a milk administration group (one-time administration) of a plurality of rats was fixed by a conventional method, and subjected to immunohistological staining. In the rats, a sample was collected at two locations: an administration site and a (distal) site 10 mm away from the administration site, five weeks and eight weeks after administration. In the patients, a half of the head was treated, and the other half of the head was untreated. A 3 mm-punch-diameter section including a region from the scalp surface to the top of the scull periosteum or the top of the temporal fascia of the patient was fixed. Primary antibodies and secondary antibodies used for staining in this Example are as follows.

TABLE 5

Primary antibodies and secondary antibodies used for immunohistological staining of rat specimens

|  | Designation | Product No. | Lot | Manufacturer | |
| --- | --- | --- | --- | --- | --- |
| Ki-67 | | | | | |
| Primary | Monoclonal Mouse Anti-Rat Ki-67 Antigen (clone: MIB-5) | M7248 | 20030236 | DaKo | Denmark |
| Secondary | LSAB2 System-HRP for use on Rat Specimens | K0609 | — | DaKo | Denmark |
| CD68 | | | | | |
| Primary | Mouse ANTI RAT CD68 (clone: ED1) | MCA341R | 1014 | BIO-RAD | USA |
| Secondary | LSAB2 System-HRP for use on Rat Specimens | K0609 | — | DaKo | Denmark |
| PPAR γ | | | | | |
| Primary | PPAR γ (C26H12) Rabbit mAb | #2435 | No. 4 | Cell Signaling Technology | USA |
| Secondary | EnVision + System-HRP Labelled Polymer Anti- Rabbit | K4003 | — | DaKo | Denmark |

Figure 7:
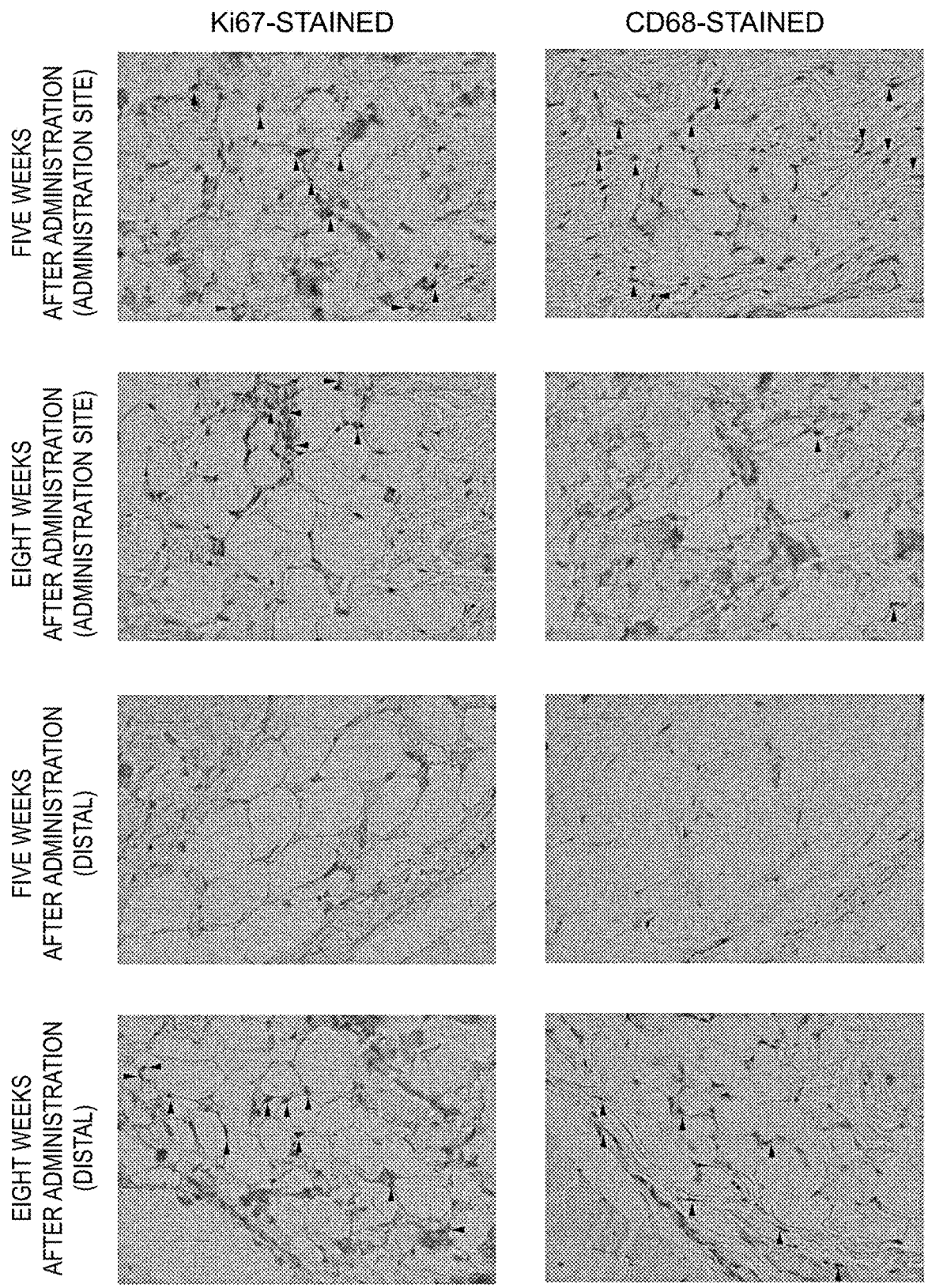
FIG. 7 shows the results of immunohistological staining of Wistar rat dorsal subcutaneous fat layer tissues (staining of Ki67-positive fat cells and staining of CD68-positive macrophages) after administration of milk.

FIG. 7 shows the results. As shown in FIG. 7, the number of Ki67-positive fat cells and the number of CD68-positive macrophages increased five weeks after administration, and decreased eight weeks after administration. On the other hand, distally, the positive cells were not observed five weeks after administration, and the Ki67-positive cells and the CD68-positive macrophages came to be observed eight weeks after administration.

This revealed that administration of milk increased the number of Ki67-positive fat cells, i.e. activated fat cells to vitalize division of the cells, and increased the number of macrophages in tissues. From microscope images, Ki67-positive fat cells were considered to be mainly fat cells and fat stem cells. However, the number of Ki67-positive fat cells and the number of macrophages decreased eight weeks after administration. On the other hand, surprisingly, the number of Ki67-positive fat cells and the number of CD68-positive macrophages increased even distally later than at the administration site. This indicates that the effect of administration of milk is propagated through tissues.

Similar experiments were conducted on humans. Human tissues were stained with CD34, CD68, CD163 and PPAR-γ in addition to CD31.

TABLE 6

Primary antibodies and secondary antibodies used for immunohistological staining of human specimens

| | Designation | Product No. | Lot | Manufacturer | |
|---|---|---|---|---|---|
| CD31 | | | | | |
| Primary | Monoclonal Mouse Anti-Human CD31 | M0823 | 000083027 | DaKo | Denmark |
| Secondary | EnVision + System-HRP Labelled Polymer Anti-Mouse | K4001 | — | DaKo | Denmark |
| CD34 | | | | | |
| Primary | Monoclonal Mouse Anti-Human CD34 | M7165 | 00048997 | DaKo | Denmark |
| Secondary | EnVision + System-HRP Labelled Polymer Anti-Mouse | K4001 | — | DaKo | Denmark |
| CD68 | | | | | |
| Primary | CD68 Mouse monoclonal antibody | MCL-CD68-KP1 | 211710 | NOVOCASTRA | England |
| Secondary | EnVision + System-HRP Labelled Polymer Anti-Mouse | K4001 | — | DaKo | Denmark |
| CD163 | | | | | |
| Primary | Anti-Human Macrophage Surface Antigen Monoclonal Antibody | KT013 | TG201213 | Trans Genic Inc. | Japan |
| Secondary | EnVision + System-HRP Labelled Polymer Anti-Mouse | K4001 | — | Dako | Denmark |
| PPAR γ | | | | | |
| Primary | PPAR γ (C26H12) Rabbit mAb | #2435 | No. 4 | Cell Signaling Technology | USA |
| Secondary | EnVision + System-HRP Labelled Polymer Anti-Rabbit | K4003 | — | Dako | Denmark |

Figure 8A:
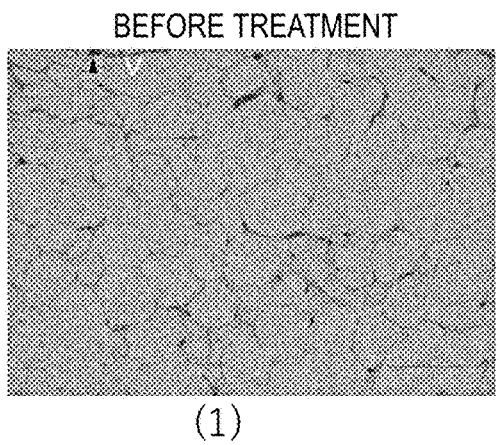
FIG. 8A shows the results of immunohistological staining of scalp fat layer tissues (CD31 staining and CD34 staining) after administration of milk.
Figure 8A:
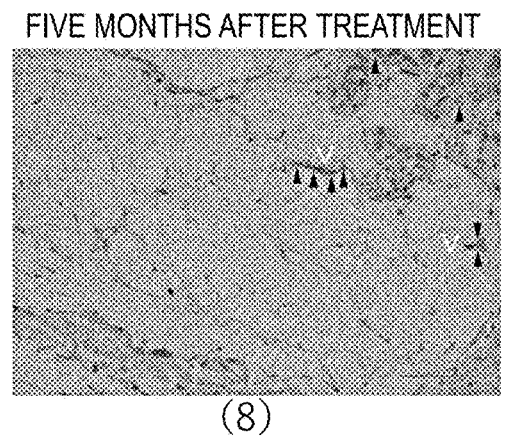
Figure 8A:
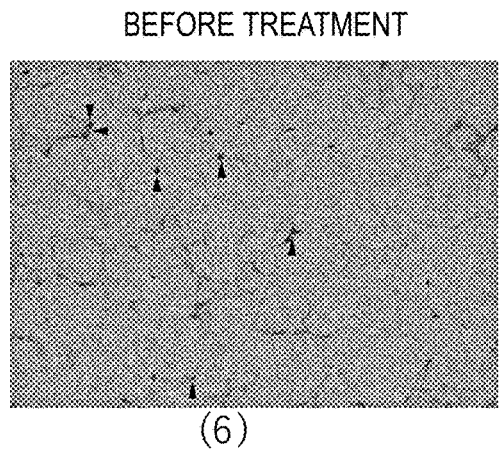
Figure 8A:

FIG. 8A shows CD31 staining and CD34 staining. CD31-positive cells were observed only on the vascular endothelium. On the other hand, CD34-positive cells were observed in regions other than blood vessel. This indicated that administration of milk increased the number of CD31-negative CD34-positive cells at the administration location. As shown in FIG. 8A, the number of CD-positive cells per unit area five months after single treatment was larger than that before the treatment (49-year-old female). The number of CD34-positive cells was 106.7 on average (n=3) on the untreated side, and 129.7 on average (n=3) on the treated side over the entire 3 mm-punch section, and in all the patients, the number of CD34-positive cells increased on the treated side. CD34-positive cells are known as a fat stem cell marker, and increase in the number of CD34-positive cells indicates increase in the number of fat stem cells. Therefore, these results revealed that fat tissues at the milk administration site were modified to produce fat stem cells.

Figure 8B:
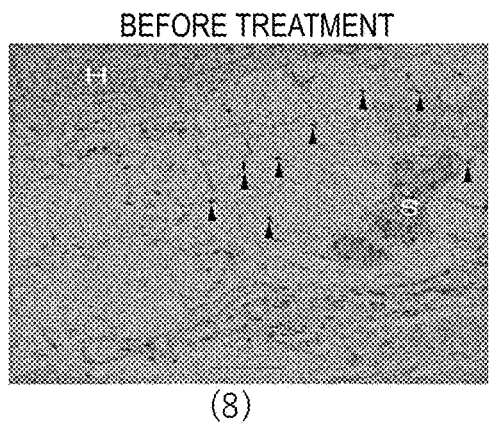
FIG. 8B shows the results of immunohistological staining of scalp fat layer tissues (staining of CD68-positive macrophages, staining of CD163-positive tissue-resident M2-like macrophages and staining of PPAR-γ-positive cells) after administration of milk.
Figure 8B:
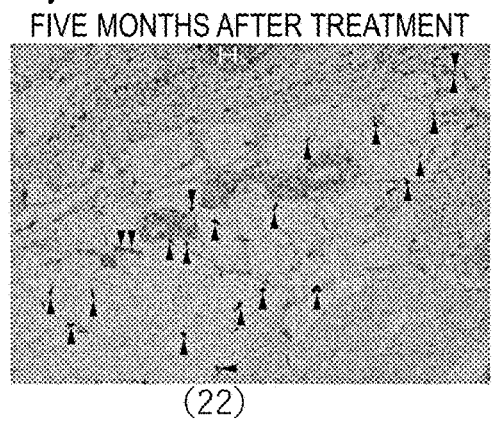
Figure 8B:
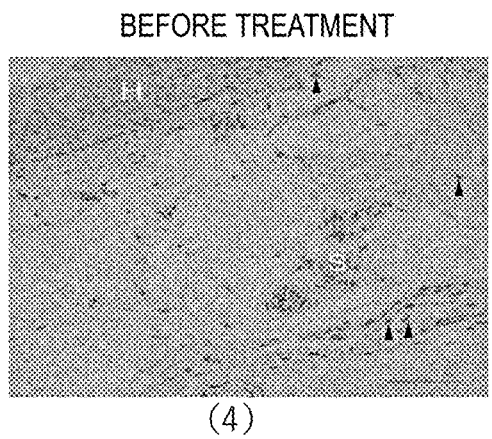
Figure 8B:
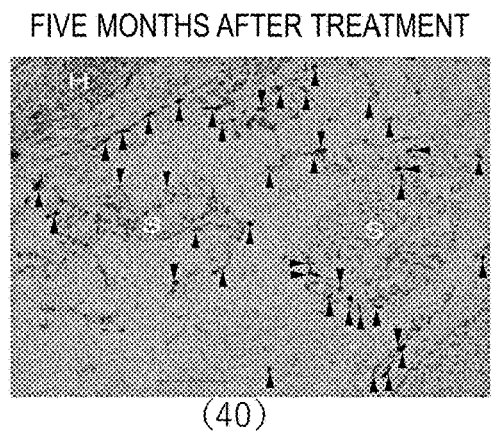
Figure 8B:
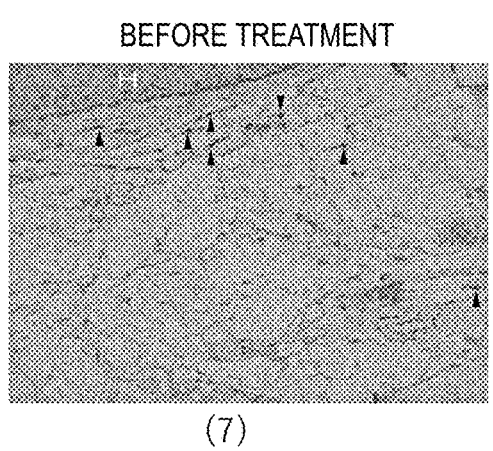
Figure 8B:
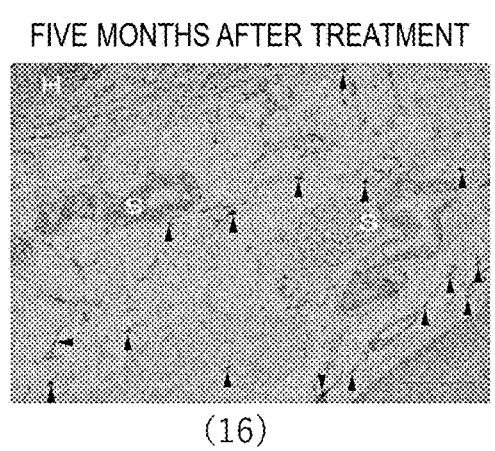

FIG. 8B shows the results of staining of CD68-positive macrophages and PPAR-γ-positive cells. As shown in FIG. 8B, administration of 20 μL of milk increased the numbers of CD68-positive macrophages, CD163-positive macrophages and PPAR-γ-positive cells per unit area in the human (49-year-old female). In the male patient (50-year-old) after passage of fifteen months after the start of treatment (four-time administration), administration of milk increased the numbers of CD68-positive macrophages, CD163-positive macrophages and PPAR-γ-positive cells per unit area on the treated side.

Thus, at the milk administration site, the number of tissue-resident M2-like macrophages increased, which indicates contribution of immature fat cells being PPAR-γ-positive cells.

In FIGS. 8A and 8B, symbol "H" denotes a hair follicle, symbol "V" denotes a blood vessel, and symbol "S" denotes a sebaceous gland.

Example 8: Examination of Change in Tissues with Lactoferrin (Forced Oral Ingestion in Large Amount)

Figure 9:
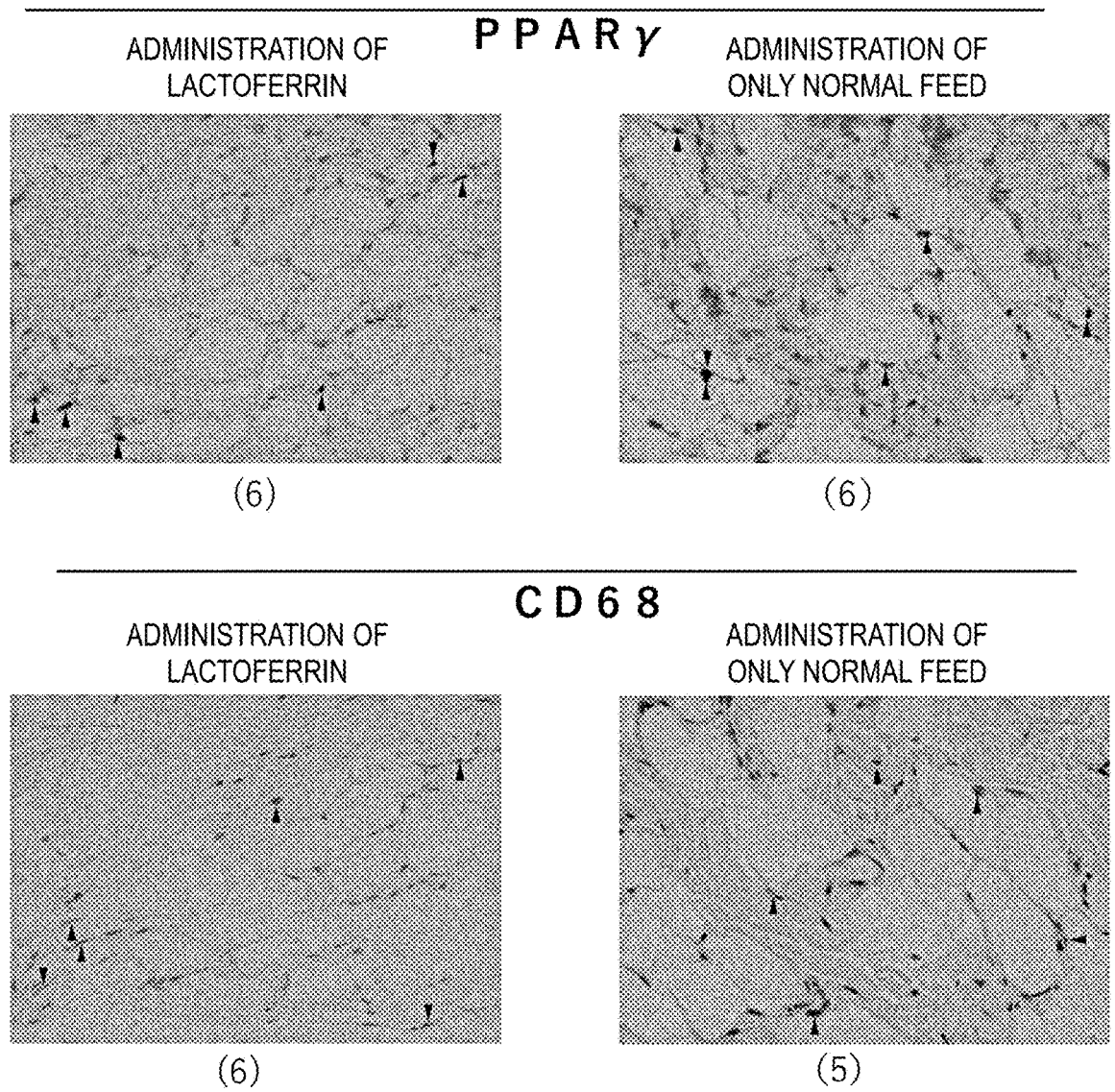
FIG. 9 shows the results of immunohistological staining of rat dorsal subcutaneous fat layer tissues (staining of CD68 and PPAR-γ-positive cells) after oral administration of lactoferrin.

As a comparative test, lactoferrin was administered instead of milk, and whether the number of CD68-positive cells and the number of PPAR-γ-positive cells increased or not was examined. As lactoferrin, three tablets of Nice rim essence 62971 (manufactured by Lion Corporation) corresponding to 300 mg of active lactoferrin (amount ingested per day by a human) were orally administered to a 12-week-old Wistar rat (n=3). Administration was performed once a day with the tablets injected (forcedly ingested) into the stomach using a feeding needle. Eight weeks after administration, a paraffin-embedded section of the dorsal skin was prepared by a conventional method, and subjected to immunohistological staining. FIG. 9 shows the results.

As shown in FIG. 9, either the number of CD68-positive cells or the number of PPAR-γ-positive cells did not increase in administration of lactoferrin. This revealed that although administration of lactoferrin was said to have a hair increasing effect, but unlike milk, lactoferrin had no skin modification effect. Normal tissues (dorsal part) of an 18-week-old Wistar rat were stained, respectively, with an anti-CD68 antibody and a PPAR-γ antibody, and there was no significant difference between the normal tissues and the tissues eight weeks after administration of lactoferrin (20 weeks of age). It has been reported that lactoferrin suppresses the activity of PPAR-γ while suppressing differentiation of fat precursor cells into fat (see M. Yag, et al., Journal of Oral Science, 50: 419-425, 2008), and the above results are consistent with this report. Ingredients of milk other than lactoferrin were considered to contribute to rejuvenation of fat cells and increase in fat precursor cells by administration of milk.

Figure 10A:
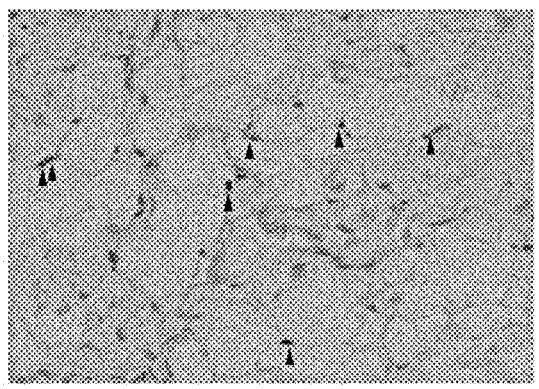
FIG. 10A shows the results of staining of CD68 and PPAR-γ-positive cells in tissues four weeks and eight weeks after administration of physiological saline. The arrowheads in the Figure, each indicate a location at which positive cells are present, and the number in parentheses in the lower right of each stained image 3 indicates the number of positive cells in the visual field.
Figure 10A:
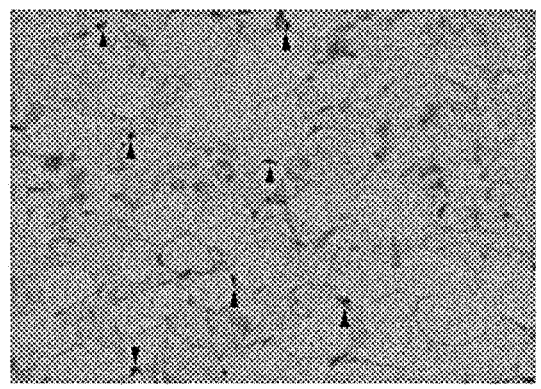
Figure 10A:
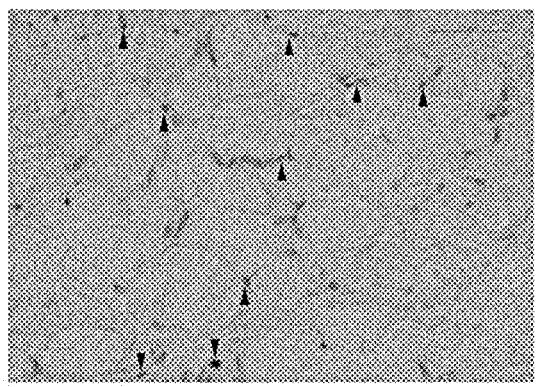
Figure 10A:
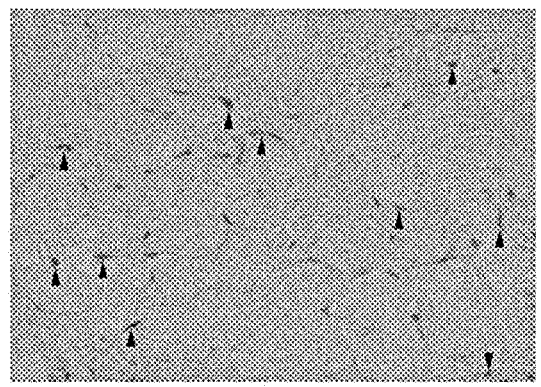

Example 9: Change in Tissues with Representative Fatty Acids Contained in Milk, and PPAR-γ Activity Next, representative fatty acids contained in milk were administered to a 12-week-old Wistar rat at a plurality of locations on the dorsal skin as in Example 1(2) above, and a change in tissues by the administration was observed after the tissues were subjected to immunohistological staining. More specifically, physiological saline was administered in an amount of 20 µL per location, an administration liquid containing 1 mg of a fatty acid was administered in an amount of 20 µL per location, and a change in CD68-positive macrophage stained images and PPAR-γ-positive cell images by the administration was observed. Samples of the Wistar rat were obtained by sampling administration sites (four weeks after administration and eight weeks after administration). FIGS. 10A to 10G show the results. FIG. 10A shows the results in a group administered physiological saline (negative control).

Figure 10C:
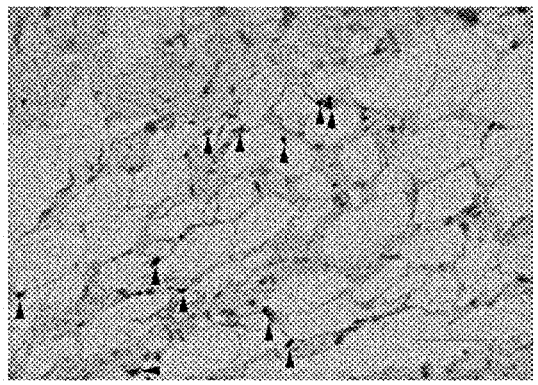
FIG. 10C shows the results of staining of CD68 and PPAR-γ-positive cells in tissues four weeks and eight weeks after administration of stearic acid. The arrowheads in the Figure, each indicate a location at which positive cells are present, and the number in parentheses in the lower right of each stained image indicates the number of positive cells in the visual field.
Figure 10C:
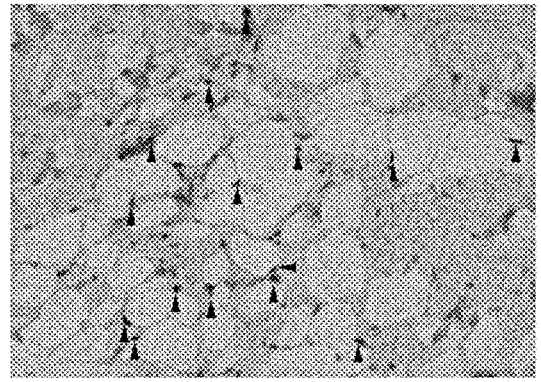
Figure 10C:
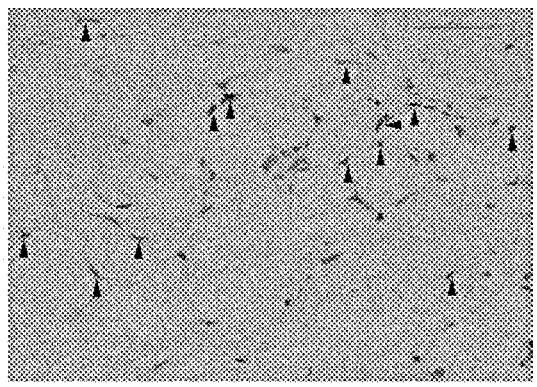
Figure 10C:
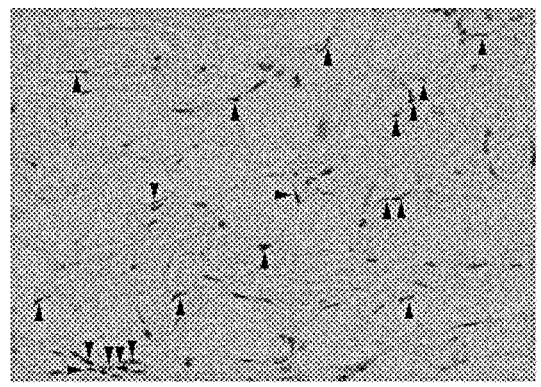
Figure 10D:
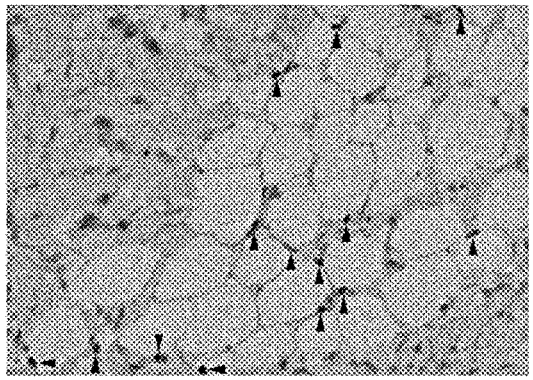
FIG. 10D shows the results of staining of CD68 and PPAR-γ-positive cells in tissues four weeks and eight weeks after administration of myristic acid. The arrowheads in the Figure each indicate a location at which positive cells are present, and the number in parentheses in the lower right of each stained image indicates the number of positive cells in the visual field.
Figure 10D:
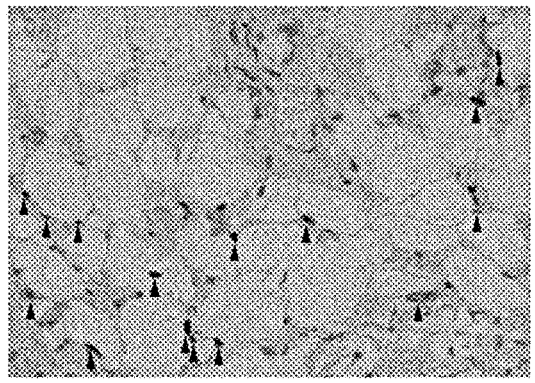
Figure 10D:
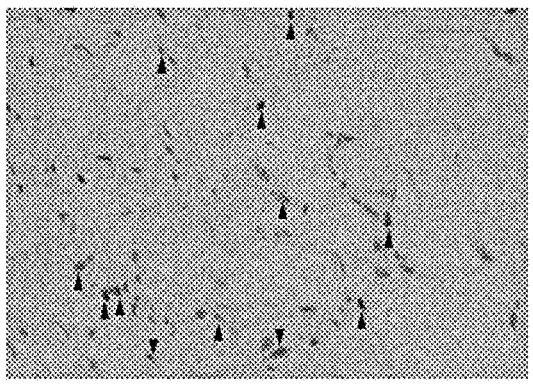
Figure 10D:
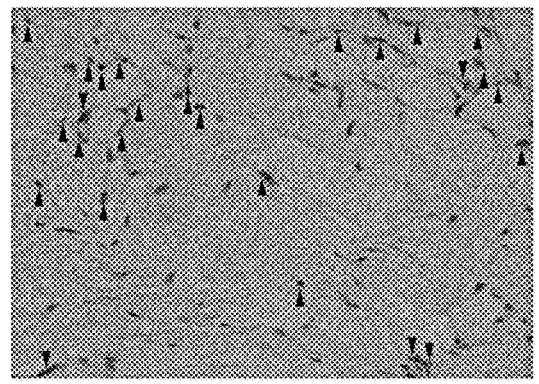

In administration of palmitic acid, stearic acid or myristic acid, the number of PPAR-γ-positive cells and the number of CD68-positive cells at the administration site increased four weeks after administration as shown in FIGS. 10B to 10D, respectively. For any of the above fatty acids, increase in the number of PPAR-γ-positive cells and the number of CD68-positive cells at the administration site was maintained eight weeks after administration of the fatty acid.

At saturated fatty acid injection sites, infiltration of a large number of CD68-positive cells was observed, and fibrillization of normal tissues was observed. Therefore, in FIGS. 10B to 10D, a change in fat tissues was examined at a location which was closest to the administration site and where normal tissues were maintained (non-fibrillization location).

Figure 10E:
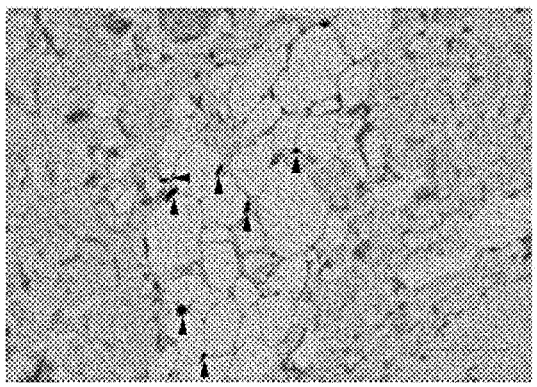
FIG. 10E shows the results of staining of CD68 and PPAR-γ-positive cells in tissues four weeks and eight weeks after administration of oleic acid. The arrowheads in the Figure, each indicate a location at which positive cells are present, and the number in parentheses in the lower right of each stained image indicates the number of positive cells in the visual field.
Figure 10E:
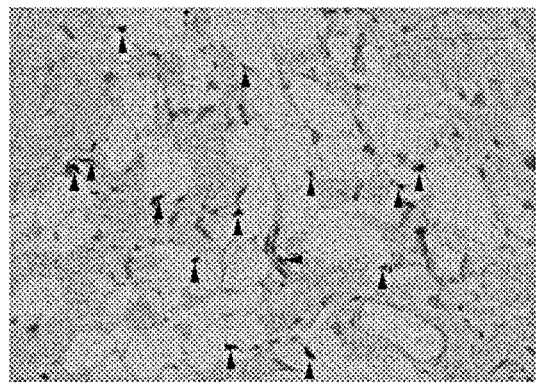
Figure 10E:
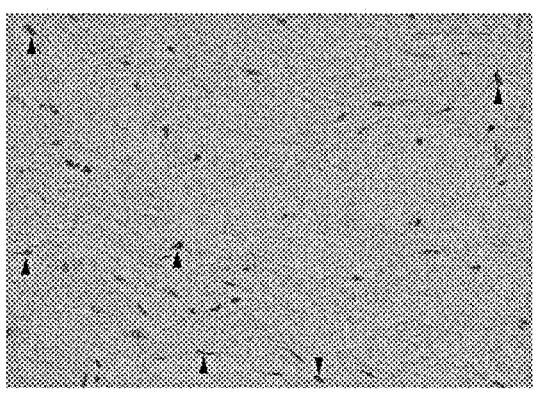
Figure 10E:
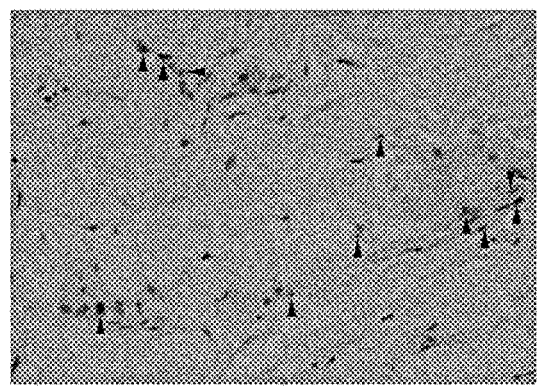
Figure 10F:
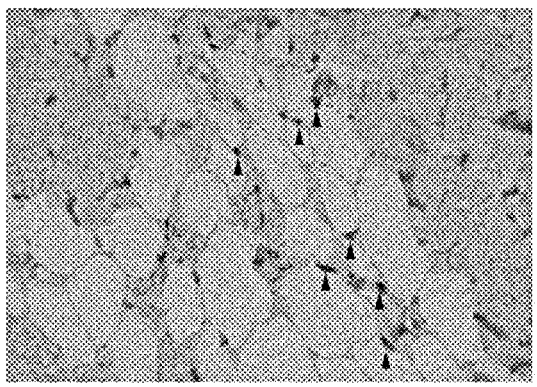
FIG. 10F shows the results of staining of CD68 and PPAR-γ-positive cells in tissues four weeks and eight weeks after administration of α-linolenic acid. The arrowheads in the Figure, each indicate a location at which positive cells are present, and the number in parentheses in the lower right of each stained image indicates the number of positive cells in the visual field.
Figure 10F:
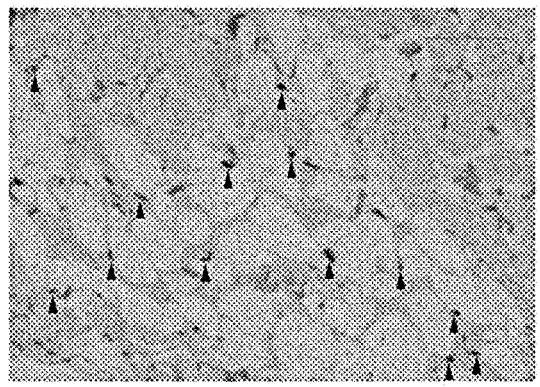
Figure 10F:
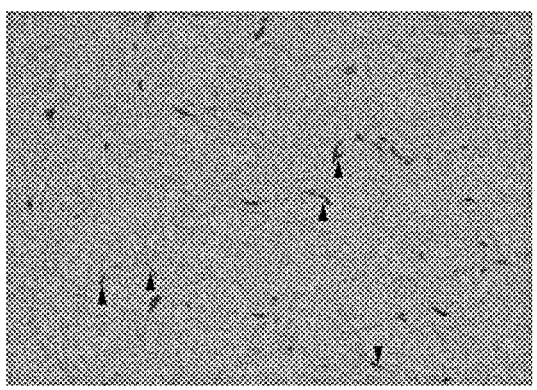
Figure 10F:
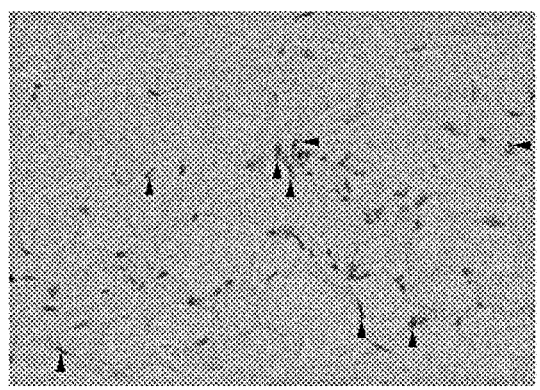
Figure 10G:
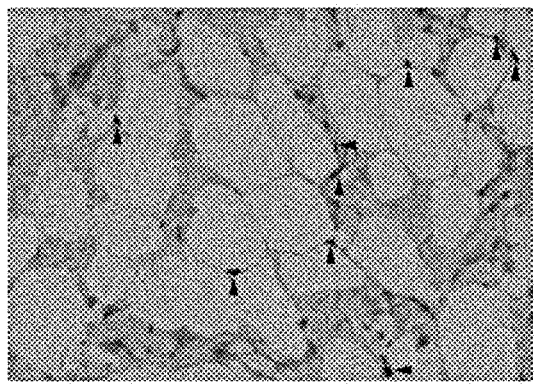
FIG. 10G shows the results of staining of CD68 and PPAR-γ-positive cells in tissues four weeks and eight weeks after administration of linoleic acid. The arrowheads in the Figure, indicate a location at which positive cells are present, and the number in parentheses in the lower right of each stained image indicates the number of positive cells in the visual field.
Figure 10G:
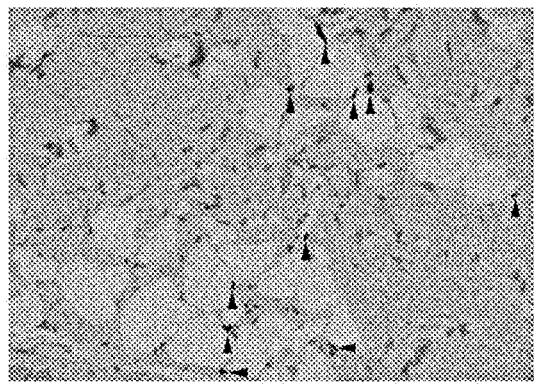
Figure 10G:
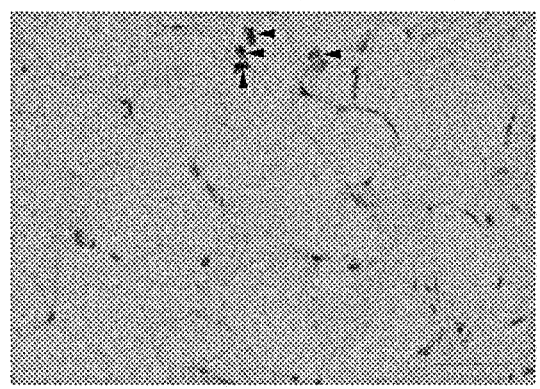
Figure 10G:
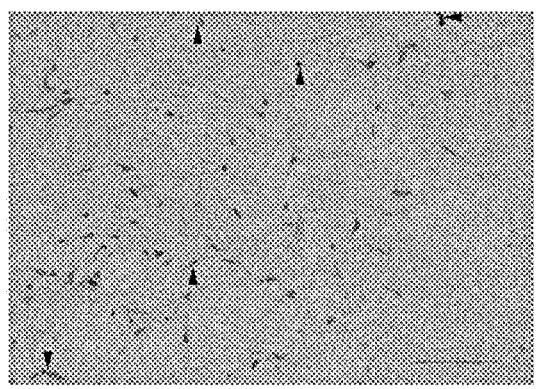

In administration of oleic acid, α-linolenic acid or linoleic acid, the number of PPAR-γ-positive cells and the number of CD68-positive cells did not remarkably increase as compared to the control four weeks after administration, and the number of CD68-positive cells increased eight weeks after administration, as shown in FIGS. 10E to 10G. On the other hand, in administration of oleic acid, α-linolenic acid or linoleic acid, the number of CD68-positive cells did not greatly increase (a weak effect was observed overall). CD68-positive cells were differentiated into tissue-resident M2-like macrophages by PPAR-γ to promote homeostasis of tissues. In administration of a saturated fatty acid such as palmitic acid, stearic acid or myristic acid, the number of CD68-positive cells and the number of PPAR-γ-positive cells increased, and therefore the number of tissue-resident M2-like macrophages was considered to increase in tissues where the fatty acid was administered. On the other hand, in administration of an unsaturated fatty acid, the number of PPAR-γ-positive cells increased, but the number of CD68-positive cells did not greatly increase, and thus it was considered that the tissue-resident M2-like macrophage induction effect was limited. These results were consistent to the fact that in Example 6 above, saturated fatty acids exhibited a high wound healing-promoting effect, whereas the wound healing-promoting effect of unsaturated fatty acids was limited. Since the PPAR-γ activity of macrophages has been reported to greatly contribute to the function of fatty acids (see Odegaard J I, et al., Nature, 447: 1116-1121, 2007), the increase in the number of CD68-positive cells and the number of PPAR-γ-positive cells in fat tissues by administration of a saturated fatty acids were the results which supported the view that administration of a saturated fatty acid modified the skin. Increase in the number of PPAR-γ-positive fat cells was confirmed from increase in the number of PPAR-γ-positive cells having fat droplets in the cells, and this result indicated that administration of a saturated fatty acid activated PPAR-γ-positive fat stem cells.

Palmitic acid, stearic acid or myristic acid is a saturated fatty acid, and oleic acid, α-linolenic acid or linoleic acid is an unsaturated fatty acid. The results in FIGS. 10B to 10G show that a saturated fatty acid had an effect of inducing expression of PPAR-γ-positive cells (including immature fat cells) to tissues early, and an unsaturated fatty acid had an effect of inducing expression of PPAR-γ-positive cells (immature fat cells) later. From these results, it is considered that a saturated fatty acid induces intense tissue inflammation to integrate macrophages, and while integrating macrophages into tissues, the saturated fatty acid increases the number of PPAR-γ-positive cells to suppress the induced inflammation. On the other hand, it is considered that an unsaturated fatty acid was less capable of integrating macrophages into tissues, and an inflammation suppression effect of PPAR-γ was dominant.

Fatty acids are known to promote secretion of inflammatory cytokines (see Hotamisligil G. S., Nature, 542:177-185, 2017). The results of this Example show that while inducing intense inflammation reaction, a saturated fatty acid promoted tissue regeneration by increasing the number of PPAR-γ-positive cells to depress the inflammation. This indicates that PPAR-γ-positive cells grown in tissues by administration of saturated fatty acid may induce fat stem cells and immature fat cells, and induce M2 macrophages, leading to the occurrence of wound healing reaction and tissue regeneration. It has been confirmed that expression of PPAR-γ and action thereof on macrophages activate immune cells (particularly derive M1 macrophages to M2 macrophages) (see Croadell A. et al., PPAR Research, ID 549691, 2015).

Example 10: Relationship Between Improvement of Scalp and Hair Quality Improvement Effect and Hair Increase Effect Examples 1 to 9 above revealed that administration of milk regenerated and modified the scalp or skin to exhibit a hair quality improvement effect.

In this Example, hairs having a high growth rate were given attention in view of the results of Examples above, and the effect of administration of milk was evaluated. Specifically, hairs growing by 0.9 mm or more per 3 days were selected from a scalp image, and the sum of gained lengths was calculated. Adult hair is known to grow at a rate of about 10 mm a month (i.e. a rate of about 1 mm per 3 days).

For this purpose, hair on a part of the scalp of each of a plurality of adults given milk in an amount of 20 µL/location (six patients were treated by one-time administration, and one patient was treated over four months at an interval of once a month) was shaven, the hair-shaven site was imaged after three days, and image analysis was performed. Hair on the same location was shaven again one year after administration, the hair-shaven site was imaged after three days, and image analysis was performed. After hair shaving, hair had a length of 0.4 mm on average. In the following, the sum of gained lengths for hairs having a length of 1.4 mm or more was calculated three days after hair shaving.

FIGS. 11A and 11B show the results of counting the lengths of hair portions of the patients using image software. Here, as representative measurement examples, FIG. 11A shows the comparative counting results in the course of treatment for patient A (50-year-old male, treated over four months at an interval of once a month, after passage of one year after the start of treatment), and FIG. 11B comparative measurement results on the untreated side and the treated side for two patients (patient A and patient B (47-year-old female, treated only one administration, after passage of one year after treatment)).

In FIG. 11A, measurement results before treatment and one year after the start of treatment of patient A are compared. FIG. 11A shows the sum of the lengths of hairs having a length of 1.4 mm or more three days after hair shaving (1.4 mm or more) and the sum (all) of the lengths of all hairs including hairs having a length of 0.9 mm or more and less than 1.4 mm three days after hair shaving. In patient A, the sum of the lengths of hairs having a length of 1.4 mm or more after three days was 311.9 before treatment, and 337.9 one year after the start of treatment. The sum of the lengths of all hairs three days after hair shaving was 405.7 before treatment, and 419.2 one year after the start of treatment.

In FIG. 11B, the measurement results on the untreated side and the treated side one year after the start of treatment for patients A and B are compared. FIG. 11B shows the sum of the lengths of hairs having a length of 1.4 mm or more three days after hair shaving (1.4 mm or more) and the sum (all) of the lengths of all hairs including hairs having a length of 0.9 mm or more and less than 1.4 mm three days after hair shaving. In patient A, the sum of the lengths of hairs having a length of 1.4 mm or more three days after hair shaving was 199.4 on the untreated side and 337.9 on the treated side. In patient B, the sum of the lengths of hairs having a length of 1.4 mm or more three days after hair shaving was 114.3 on the untreated side and 300.7 on the treated side.

Similarly, in patient A, the sum of the lengths of hairs having a length of 0.9 mm or more three days after hair shaving was 357.8 on the untreated side and 419.2 on the treated side. In patient B, the sum of the lengths of all hairs three days after hair shaving was 261.5 on the untreated side and 378.1 on the treated side.

As a negative control, physiological saline was injected on a half of the head. A change in hair (the number of hairs having a length of 1.4 mm or more) by injection of physiological saline on a half of the head was observed every month over six months, and the result showed that the ratio of change before treatment and six months after treatment was −0.84% to +1.24%, with the average being 1.03%. On the treated side where physiological saline was injected, and the untreated side, the change six months after treatment was −0.99% to +1.25%, with the average being 1.06% (n=4). A change in hair (the sum of the lengths of hairs having a length of 1.4 mm or more) by injection of physiological saline on a half of the head was observed every month over six months, and the result showed that the change before treatment and six months after treatment was −0.79% to +1.33%, with the average being 1.05%. On the treated side where physiological saline was injected, and the untreated side, the change six months after treatment was −0.95% to +1.28%, with the average being 1.07% (n=4). Thus, in the group given physiological saline as a negative control, there was no increase in hair having a length of 1.4 mm or more three days after hair shaving.

Thus, it was evident that administration of milk (20 µL/location administration) modified the scalp, and accordingly improved the growth rate of hair.

Hair having a length of 1.4 mm or more after three days was examined, and image analysis revealed that the hair was thicker than hair having a low growth rate (hair having a length of less than 1.4 mm after three days). Specifically, the thickness of hair having a length of 2.1 to 2.2 mm was 97.42 µm on average, whereas the thickness of hair having a length of less than 1.4 mm was 75.39 µm on average. These results revealed that administration of milk (20 µL/location) increased thick hair having a high growth rate.

In administration of milk, the improvement of tension and stiffness of hair was observed (the tension and stiffness of hair improved and increase in the volume of hair was observed), and this was consistent with increase in thick hair.

Thus, in subjects given milk, increase in hair was observed, and modification of the scalp by administration of milk led to improvement of the growth rate of hair, and increase in thick hair having stiffness and tension and good quality.

Example A11: Osteogenesis Promoting Action

In this Example, the effect of administration of palmitic acid on osteogenesis was examined.

Formation of bone defect: Hair on the head of Wistar rats (male) (four 12-week-old rats and one 18-week-old rat) was shaven with hair clippers, tangent lines were diagonally drawn above an eye and in front of an ear auricle on an opposite side, and a skull bone defect with a diameter of 8.8 mm was formed on the rear side from the intersection of the lines. The skull bone defect was formed by performing 1. general anesthesia, 2. skin incision, 3. periosteum separation and 4. scull bone cutting (diameter: 8.8 mm) in this order. The skull bone defect was formed by gradually chipping a surrounding bone with a trephine bur and a microdrill, and finally drawing up the bone.

Observation of osteogenesis: A hydroxyapatite thin film shaped to fit the size of the bone defect part was placed on the bone defect part. Here, 0.02 mg (20 µg) of palmitic acid was applied to the sheet. Specifically, 0.02 mL (20 µL) of a solution obtained by dissolving 1 mg of palmitic acid in 1 mL of a solvent was dropped to the thin film, and dried to be placed on the bone defect part.

The animals were reared for eight weeks, tissues were then collected, and the animals were then killed. The tissues were perfused and fixed. A transverse cross-section of the skull bone was subjected to hematoxylin-eosin staining, and observed with a microscope. Thereafter, the areas of portions where osteogenesis was observed were compared between a sample with a thin film coated with palmitic acid and a sample with an uncoated thin film. Image J was used for analysis.

3D-CT images of the skull bone were acquired using the following system.

Apparatus: ScanXmate-E090 manufactured by Comscantecno Co., Ltd.

Photographing Conditions:
X-ray tube voltage: 88 kV
X-ray tube current: 89 μA
Resolution: 30.649 μm/pixel Three-dimensional reconstruction was performed using VGSTUDIO MAX (VOLUME GRAPHICS INC.).

Figure 12:
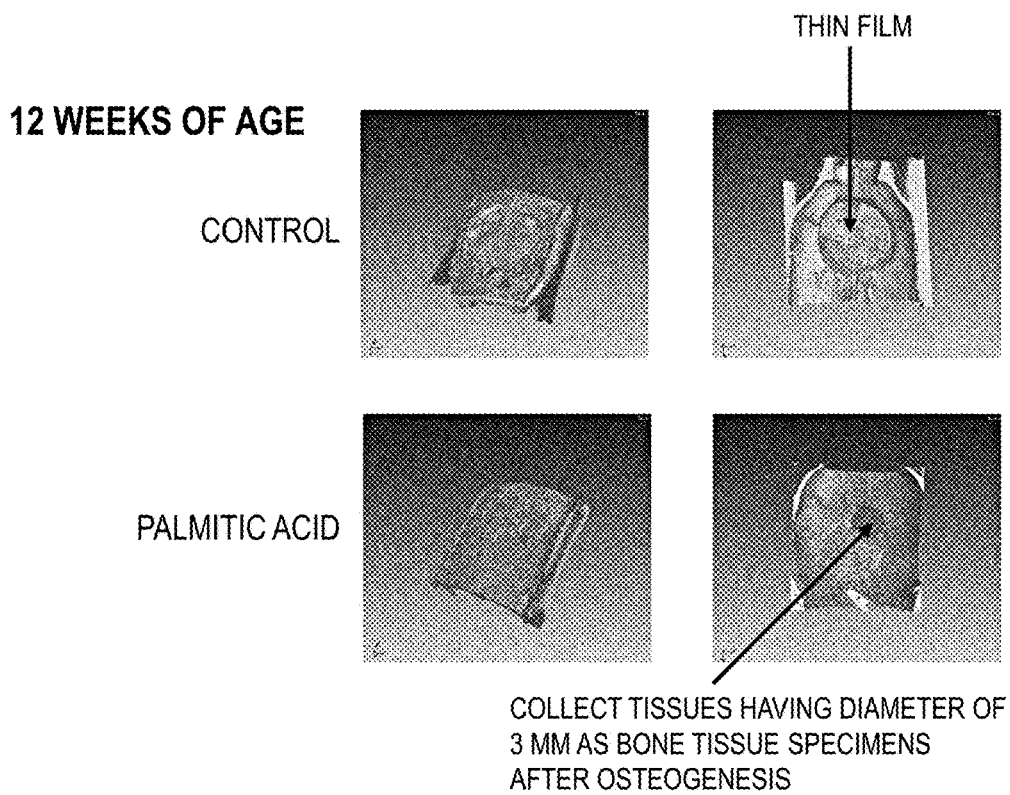
FIG. 12 is an image of osteogenesis observed by 3D-CT after a biocompatible film coated with palmitic acid or an uncoated biocompatible film is placed on a bone resection site (diameter: 8.8 mm). For sampling tissues, a hole with a diameter of 3 mm is artificially bored in part of the bone after osteogenesis.

FIG. 12 shows the results. As shown in FIG. 12, the skull bone was almost completely closed by formation of a new bone when a thin film coated with palmitic acid was used, whereas formation of a new bone was insufficient when an uncoated thin film was used.

Figure 13:
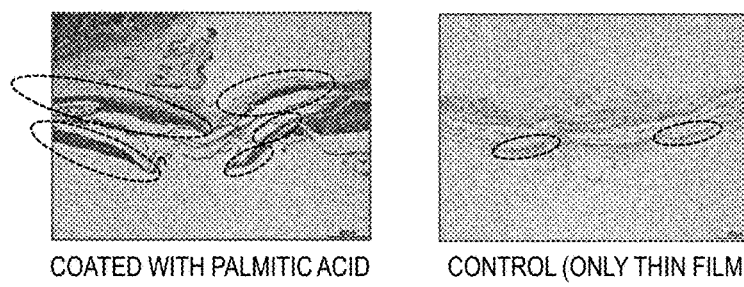
FIG. 13 is hematoxylin-eosin-stained images of bone sections obtained by sampling tissues after osteogenesis. The dashed ellipses each indicate a bone newly formed on the bone resection site, and numerical values each indicate the area of the formed bone (the number of pixels and $mm^2$).

Next, FIG. 13 shows hematoxylin-eosin-stained sections. As shown in FIG. 13, a bone stained red (see dashed lines) was formed in a large amount when a thin film coated with palmitic acid was placed, whereas a bone stained red (see dashed lines) was formed in a small amount when a thin film was placed. The stained area (the number of pixels and $mm^2$) of the osteogenesis part in the tissue section was 12,132 pixels (0.984 $mm^2$) for the palmitic acid-coated thin film, and 1,025 pixels (0.083 $mm^2$) for the control. The formed bone was remarkably thicker for the palmitic acid-coated thin film than for the control thin film.

This revealed that palmitic acid had osteogenesis promoting action.

At the time of killing the animals, bone tissue fragments (diameter: 3 mm) were collected.

The animals were reared for eight weeks, and tissues were collected, perfused and fixed. The bone tissues were collected with a trephine bur (diameter: 3 mm) when osteogenesis was sufficient, and an existing bone and a regenerated bone of an open bone margin portion were collected with bone forceps (Luer forceps) for specimens (rats) in which osteogenesis was insufficient.

The collected tissue fragments were immersed in an RNA stabilization solution (Thermo Fisher Scientific, Lithuania), and frozen with liquid nitrogen, and stored at −80° C. Total RNA was purified and extracted from the stored tissue fragments by using a spin column in accordance with a protocol accompanying a kit after 25 mg of tissue fragments were encapsulated in a sample tube together with five stainless beads (diameter: 3 mm), and the tissue fragments were homogenized using RNeasy Mini Kit (QIAGEN GmbH, Hilden, Germany) and TissueLyser II (QIAGEN GmbH, Hilden, Germany). Analysis of gene expression by quantitative PCR was performed in the following manner: Integrated FNA technologies, Inc (Skokie, IL, USA) was requested to design and synthesize gene-specific primers and probes, and using PrimeTime Gene Expression Master Mix Reagent (Integrated DNA Technologies, Inc, Skokie, IL, USA) and Rotor-Gene Q PCR Apparatus (QIAGEN GmbH, Hilden, Germany), PCR analysis was performed twice per gene per specimen to analyze the expression level of a target gene. Information of seven rat genes used for gene expression analysis by quantitative PCR (qPCR; ΔΔCt method), and nucleotide sequences of synthesized probes and primer sets are as follows.

```
1.) Ribosomal protein lateral stalk subunit P0 (RplP0),
Rattus norvegicus: mRNA, 1,093 bp, NM_022402.2, GI:
310616731
6-FAM/CCT GTC TTC /ZEN/CCT GGG CAT CAC G/IABkFQ

CAA TCC CTG ACG CAC CG

TGT CTG CTC CCA CAA TGA AG

2.) C-X-C motif chemokine ligand 12 (Cxcl12), transcript
variant 1, Rattus norvegicus: mRNA 1,880 bp NM_022177.3
GI: 7649650
56-FAM/TCA ACA CTC /ZEN/CAA ACT GTG CCC TTC A/3IABkFQ

GAG CCA ACG TCA AAC ATC TG

GGC TTT GTC CAG GTA CTC TTG

3.) C-X-C motif chemokine receptor 4 (Cxcr4), Rattus
norvegicus: mRNA 1,726 bp NM_022205.3 GI: 82617587
56-FAM/CAA TGC TCG /ZEN/CTC TCC AGC CCT /3TABkFQ

CGT TTG GTG CTC CGG TAG

TCT CCA GAC CCT ACT TCT TCG

4.) Integrin subunit alpha 4 (Itga4), Rattus norvegicus
mRNA 3,736 bp NM_001107737.1 GI: 157819948
56-FAM/CGA AGG AGG /ZEN/TCA AAT GAG CCA GTC A/3IABkFQ

GCA TCT CCT CTA CAT ACT CAC AG

CAC CAA CCG CTA CAT CAA CA

5.) CD34, Rattus norvegicus: CD34 molecule (Cd34), mRNA
1,161 bp NM_001107202.2 GI: 169790781
56-FAM/TCC CTG GAA /ZEN/GTA CCA GCC ACT ACT /3IABkFQ

GGA GTA TTT CCA CCA GTT CCT AC

GAT GGC TGG TGT GGT CTT ATT
```

-continued

6.) Bone morphogenetic protein-4 (BMP4), Rattus
norvegicus: mRNA 1,559 bp NM_012827.2 GI: 148747215
56-FAM/CCT TGT TTT /ZEN/CTG TCA AGA CAC CAT GAT TCC
/3IABkFQ

ATA AAA CGA CCA TCA GCA TTC G

GCC TTT CCA GCA AGT TTG TTC

7.) Bone morphogenetic protein-7 (BMP7), Rattus
norvegicus: mRNA 2,448 bp NM_001191856.2 GI: 683523995
56-FAM/TGC GAT GAT /ZEN/CCA GTC CTG CCA G/3IABkFQ

CGT TCA TGT AGG AGT TCA GAG G

CTG TAT GTT AGC TTC CGA GAC C

Figure 14:
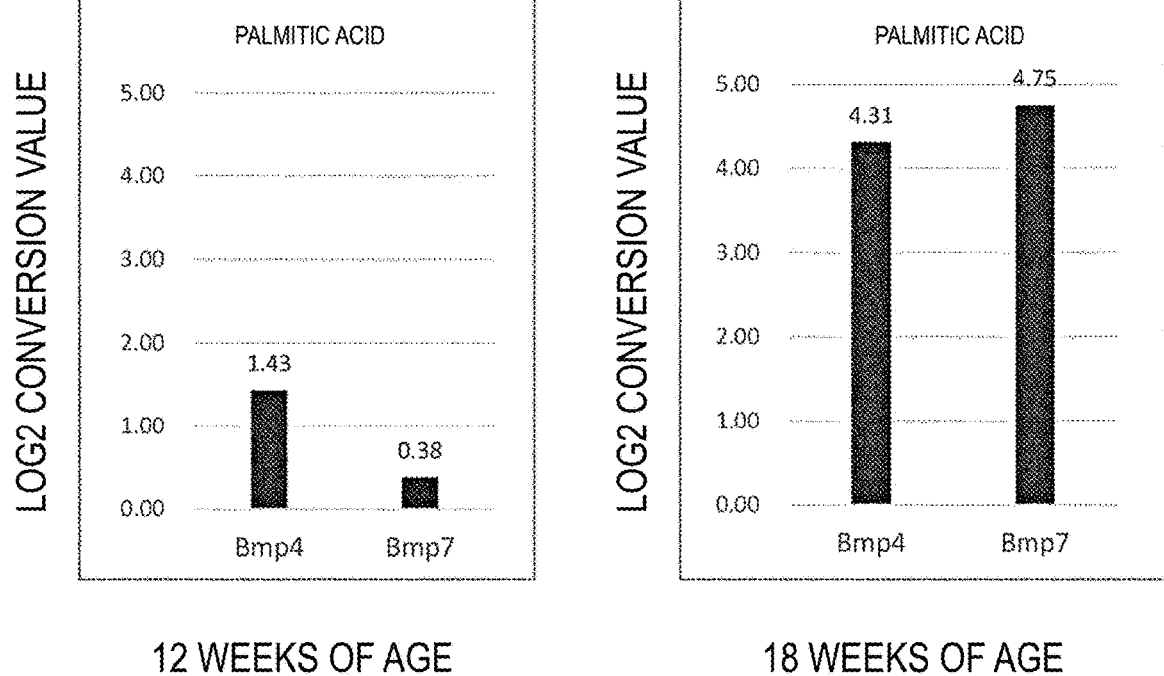
FIG. 14 shows variations in gene expression of Bone morphogenetic protein-4 (Bmp4) and Bone morphogenetic protein-7 (Bmp7) in subjects given palmitin or milk.

A difference in mRNA expression level (Ct value) between Ribosomal protein lateral stalk subunit P0 (Rp1P0) being a housekeeping gene and a target gene (average for two examinations of specimens, one 12-week-old animal and one 18-year-old animal) was compared to a difference in mRNA expression level between Rp1P0 and a target gene for a control (12-week-old animal without administration of palmitic acid), a difference between the former and the latter was converted into a gene expression ratio (factor), and the factor was further subjected to log 2 conversion, and shown in a graphic form (see FIG. 14).

As shown in FIG. 14, there was an increase in BMP4 and BMP7 important for osteogenesis as compared to the case of embedding only a thin film.

Example A12: Change in Gene Expression in Tissues after Subcutaneous Administration Next, a change in gene expression in tissues was examined. Three regions were set between the head and the tail of the dorsal part of a 12-week-old Wistar rat (male), and each region was divided between the left and the right of the backbone into two regions to set a total of six regions on the dorsal part. Milk or palmitic acid was injected in an amount of 20 µL per location at two locations in the vicinity of the center of each region. The distance between the two locations was 1 cm.

The collected tissue fragments were frozen with liquid nitrogen, and stored at −80° C. Total RNA was purified and extracted from the stored tissue fragments by using a spin column in accordance with a protocol accompanying a kit after 25 mg of tissue fragments were encapsulated in a sample tube together with five stainless beads (diameter: 3 mm), and the tissue fragments were homogenized using RNeasy Mini Kit (QIAGEN GmbH, Hilden, Germany) and TissueLyser II (QIAGEN GmbH, Hilden, Germany). Analysis of gene expression by quantitative PCR was performed in the following manner: Integrated DNA technologies, Inc (Skokie, IL, USA) was requested to design and synthesize gene-specific primers and probes, and using PrimeTime Gene Expression Master Mix Reagent (Integrated DNA Technologies, Inc, Skokie, IL, USA) and Rotor-Gene Q PCR Apparatus (QIAGEN GmbH, Hilden, Germany), PCR analysis was performed twice per gene per specimen to analyze the expression level of a target gene. A difference in mRNA expression level (Ct value) between Ribosomal protein lateral stalk subunit P0 (Rp1P0) being a housekeeping Genes and a target gene (average for three animals in two examinations of each specimen) was compared to a difference in mRNA expression level between Rp1P0 and a target gene for a control (without administration of palmitic acid or milk), a difference between the former and the latter was converted into a gene expression ratio (factor), and the factor was further subjected to log 2 conversion, and shown in a graphic form.

Figure 15:
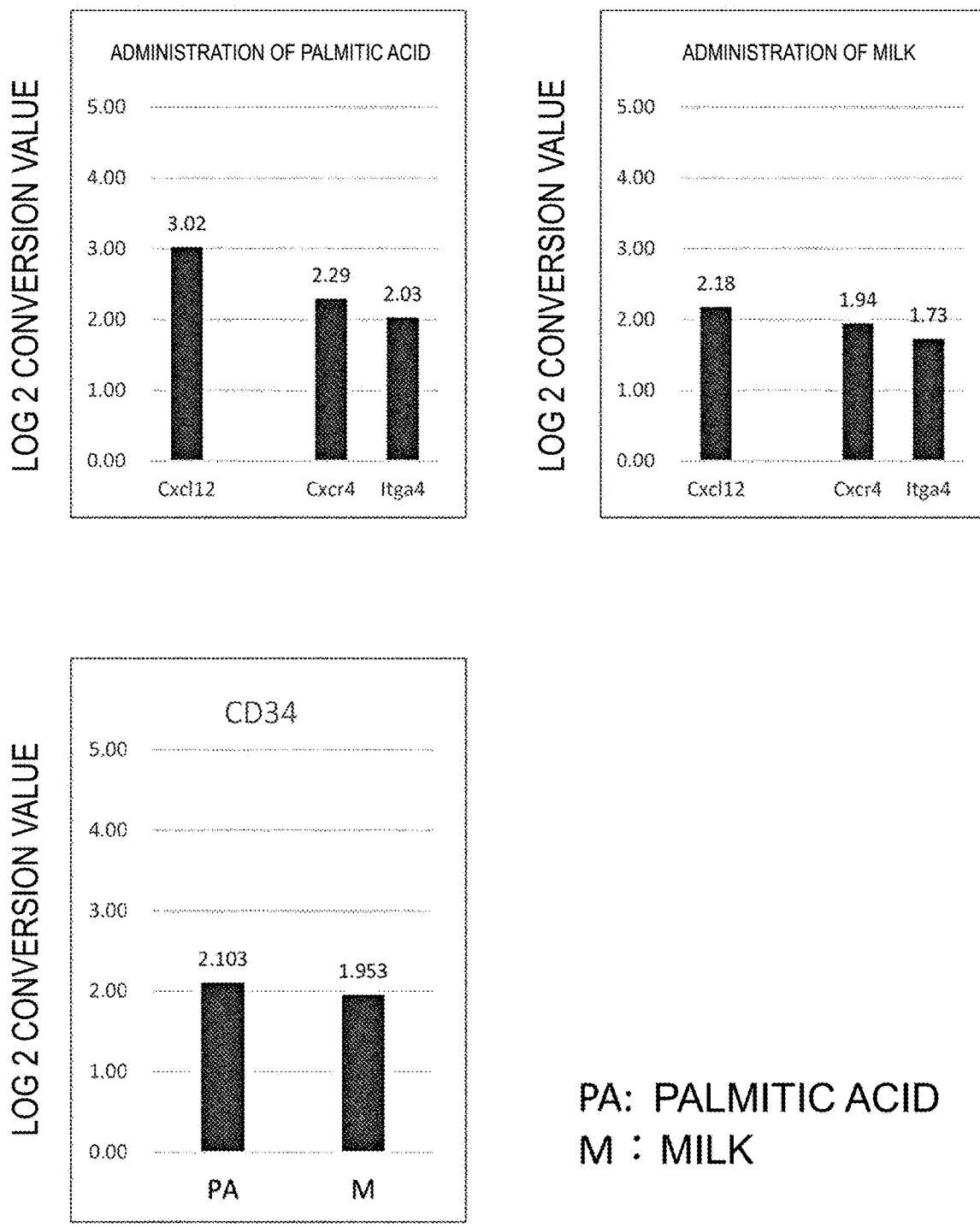
FIG. 15 shows variations in gene expression after administration of palmitic acid or milk to a control.

FIG. 15 shows the results. As shown in FIG. 15, it was revealed that either administration of palmitic acid or administration of milk greatly increased the expression levels of Cxcl12, Cxcr4 and Itga4 in tissues. Itga4 and Cxcr4 are markers that are observed in bone-marrow cells, and expression of these markers in tissues indicates that bone marrow-derived cells have been recruited into tissues. Expression of Cxcl12 indicates that at the same time these bone marrow-derived cells have been ready to be accepted. Further, as shown in FIG. 15, there was an increase in CD34 at the same time. Fat cells may be derived in the presence of the bone marrow precursor cells and macrophages.

LIST OF REFERENCES

Mirai Noro, et al., "Electrophoresis" 59: 21-24, 2015
Satoh T. et al., Nature: 495, 524-528, 2013
Festa E et al., Cell, 146: 761-71, 2011
M. Yag, et al., Journal of Oral Science, 50: 419-425, 2008
Odegaard J I, et al., Nature, 447: 1116-1121, 2007
Hotamisligil G. S., Nature, 542: 177-185, 2017
Croadell A. et al., PPAR Research, ID 549691, 2015

The invention claimed is:

1. A method for treating the roughness of cuticles of human hair of a human in need thereof, the method comprising:
intradermally or subcutaneously administering a therapeutically effective amount of a pharmaceutical composition to the scalp or to the skin of the human in need thereof, wherein the pharmaceutical composition is sterilized and comprises a therapeutically effective amount of a saturated fatty acid or a pharmaceutically acceptable salt thereof, wherein the saturated fatty acid is selected from the group consisting of palmitic acid, stearic acid and myristic acid,
wherein the pharmaceutical composition comprises a milk selected from the group consisting of milk, milk serum, a milk extracted product, a milk processed product and a mixture thereof, and
wherein the milk, milk serum, milk extracted product, milk processed product and mixture thereof comprise one or more fatty acids selected from the group consisting of palmitic acid, stearic acid and myristic acid.

2. The method of claim 1, wherein the milk has a reduced lactoferrin content.

3. The method of claim 1, wherein the milk has been sterilized by heating.

4. The method of claim 1, wherein the milk is from a human.

5. The method of claim 1, wherein the milk is from a colostrum of a female human.

6. The method of claim 1, wherein the pharmaceutical composition comprises palmitic acid.

7. The method of claim 1, wherein the pharmaceutical composition has been lyophilized.

8. A method for decreasing the number of white hairs on the scalp or skin of a human in need thereof, the method comprising:
intradermally or subcutaneously administering a therapeutically effective amount of a pharmaceutical composition to the scalp or to the skin of the human in need thereof, wherein the pharmaceutical composition is sterilized and comprises a therapeutically effective amount of a saturated fatty acid or a pharmaceutically acceptable salt thereof, wherein the saturated fatty acid is selected from the group consisting of palmitic acid, stearic acid and myristic acid,
wherein the pharmaceutical composition comprises a milk selected from the group consisting of milk, milk serum, a milk extracted product, a milk processed product and a mixture thereof, and
wherein the milk, milk serum, milk extracted product, milk processed product and mixture thereof comprise one or more fatty acids selected from the group consisting of palmitic acid, stearic acid and myristic acid.

9. The method of claim 8, wherein the milk has a reduced lactoferrin content.

10. The method of claim 8, wherein the milk has been sterilized by heating.

11. The method of claim 8, wherein the milk is from a human.

12. The method of claim 8, wherein the milk is from a colostrum of a female human.

13. The method of claim 8, wherein the pharmaceutical composition comprises palmitic acid.

14. The method of claim 8, wherein the pharmaceutical composition has been lyophilized.

* * * * *